(12) United States Patent
Sutermeister et al.

(10) Patent No.: US 10,543,035 B2
(45) Date of Patent: Jan. 28, 2020

(54) DEVICES AND METHODS FOR THERAPEUTIC HEAT TREATMENT

(71) Applicant: Boston Scientific Scimed, Inc., Maple Grove, MN (US)

(72) Inventors: Derek C. Sutermeister, Ham Lake, MN (US); Patrick A. Haverkost, Brooklyn Center, MN (US); Timothy A. Ostroot, Cokato, MN (US); Cass Alexander Hanson, St. Paul, MN (US); Jeffrey S. Lindquist, Maple Grove, MN (US); Joseph Alan Kronstedt, New Hope, MN (US); Jan Weber, Maastricht (NL); James M. Anderson, Corcoran, MN (US); Martin R. Willard, Burnsville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 952 days.

(21) Appl. No.: 14/689,363

(22) Filed: Apr. 17, 2015

(65) Prior Publication Data

US 2015/0297292 A1    Oct. 22, 2015

Related U.S. Application Data

(60) Provisional application No. 61/980,995, filed on Apr. 17, 2014, provisional application No. 61/980,952, (Continued)

(51) Int. Cl.
*A61B 18/08* (2006.01)
*A61B 18/14* (2006.01)
(Continued)

(52) U.S. Cl.
CPC ............ *A61B 18/082* (2013.01); *A61B 18/04* (2013.01); *A61B 18/14* (2013.01);
(Continued)

(58) Field of Classification Search
CPC ............ A61B 17/320725; A61B 18/04; A61B 18/082; A61B 18/14; A61B 18/1492;
(Continued)

(56) References Cited

U.S. PATENT DOCUMENTS

| 5,238,004 A | 8/1993 | Sahatjian et al. |
| 5,428,206 A * | 6/1995 | Uchida ............. G05D 23/2401 219/483 |

(Continued)

FOREIGN PATENT DOCUMENTS

| DE | 102010022926 A1 | 12/2011 |
| EP | 2671570 A2 | 12/2013 |

(Continued)

OTHER PUBLICATIONS

Wavelength Electronics. "Thermistor Basics". May 2013. Application Note AN-TC11 Rev.A. pp. 1-6.*
(Continued)

*Primary Examiner* — Lynsey C Eiseman
*Assistant Examiner* — Amanda L Steinberg

(57) ABSTRACT

Methods and devices (e.g., for nerve modulation) may include at least one thermistor and a balloon having a balloon wall. In one or more embodiments, the medical device is configured and arranged to transfer heat to the medical device surroundings. In one or more embodiments, the at least one thermistor is a portion of a thermistor array disposed on the balloon wall, the thermistor array including a plurality of thermistors and operatively engaged with a source of electric current. In one or more embodiments, the device includes at least one flexible circuit mounted on the
(Continued)

outer surface of the expandable balloon, the at least one flexible circuit including at least one temperature-sensing device that includes at least one thermistor, wherein at least a portion of a conductive layer is electronically coupled to the thermistor, with the proviso that no electrode is associated with the conductive layer.

6 Claims, 14 Drawing Sheets

Related U.S. Application Data filed on Apr. 17, 2014, provisional application No. 61/981,003, filed on Apr. 17, 2014, provisional application No. 61/980,936, filed on Apr. 17, 2014.

(51) Int. Cl.
| | |
|---|---|
| *A61M 25/00* | (2006.01) |
| *A61N 1/40* | (2006.01) |
| *A61K 41/00* | (2006.01) |
| *A61B 18/04* | (2006.01) |
| *A61K 47/69* | (2017.01) |
| *A61M 37/00* | (2006.01) |
| *A61B 18/00* | (2006.01) |
| *A61B 17/3207* | (2006.01) |
| *A61B 17/22* | (2006.01) |
| *A61B 17/00* | (2006.01) |
| *A61M 25/10* | (2013.01) |

(52) U.S. Cl.
CPC ...... *A61B 18/1492* (2013.01); *A61K 41/0052* (2013.01); *A61K 47/6957* (2017.08); *A61M 25/0043* (2013.01); *A61M 25/0082* (2013.01); *A61M 37/00* (2013.01); *A61N 1/406* (2013.01); *A61B 17/320725* (2013.01); *A61B 2017/00088* (2013.01); *A61B 2017/22061* (2013.01); *A61B 2018/00011* (2013.01); *A61B 2018/0016* (2013.01); *A61B 2018/0022* (2013.01); *A61B 2018/00125* (2013.01); *A61B 2018/00136* (2013.01); *A61B 2018/00148* (2013.01); *A61B 2018/00154* (2013.01); *A61B 2018/00178* (2013.01); *A61B 2018/00214* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00595* (2013.01); *A61B 2018/00601* (2013.01); *A61B 2018/00642* (2013.01); *A61B 2018/00714* (2013.01); *A61B 2018/00815* (2013.01); *A61B 2018/087* (2013.01); *A61B 2018/1465* (2013.01); *A61M 2025/0042* (2013.01); *A61M 2025/105* (2013.01); *A61M 2025/1081* (2013.01); *A61M 2025/1086* (2013.01)

(58) Field of Classification Search
CPC ........... A61B 2017/00088; A61B 2017/22061; A61B 2018/00011; A61B 2018/00125; A61B 2018/00136; A61B 2018/00148; A61B 2018/00154; A61B 2018/0016; A61B 2018/00178; A61B 2018/00214; A61B 2018/0022; A61B 2018/00267; A61B 2018/00404; A61B 2018/00434; A61B 2018/00511; A61B 2018/00577; A61B 2018/00595; A61B 2018/00601; A61B 2018/00642; A61B 2018/00714; A61B 2018/00815; A61B 2018/087; A61B 2018/1465; A61K 41/0052; A61K 47/48992; A61K 51/1213; A61K 51/1244; A61M 25/0043; A61M 2025/0042; A61N 1/406
USPC .................................. 606/27, 28, 29, 30, 31
See application file for complete search history.

(56) References Cited

U.S. PATENT DOCUMENTS

| | | |
|---|---|---|
| 6,508,803 B1 | 1/2003 | Horikawa et al. |
| 6,989,196 B2 | 1/2006 | Chatterjee et al. |
| 6,993,394 B2 | 1/2006 | Eggers et al. |
| 7,291,146 B2 | 11/2007 | Steinke et al. |
| 7,742,795 B2 | 6/2010 | Stone et al. |
| 7,842,281 B2 | 11/2010 | Haik et al. |
| 7,918,883 B2 | 4/2011 | Weber |
| 2003/0139787 A1 | 7/2003 | Eggers et al. |
| 2003/0236514 A1 | 12/2003 | Schwarz |
| 2004/0133223 A1 | 7/2004 | Weber |
| 2004/0136905 A1 | 7/2004 | Kent et al. |
| 2004/0167506 A1 | 8/2004 | Chen |
| 2005/0021088 A1 | 1/2005 | Schuler et al. |
| 2005/0079132 A1 | 4/2005 | Wang et al. |
| 2005/0096647 A1 | 5/2005 | Steinke et al. |
| 2008/0035348 A1 | 2/2008 | Vitek et al. |
| 2008/0188912 A1 | 8/2008 | Stone et al. |
| 2008/0213382 A1 | 9/2008 | Inkov et al. |
| 2009/0045374 A1 | 2/2009 | Lawrenz et al. |
| 2009/0081122 A1 | 3/2009 | Rufenacht et al. |
| 2010/0099941 A1 | 4/2010 | Haik et al. |
| 2011/0034974 A1 | 2/2011 | Munoz Marquez et al. |
| 2011/0068290 A1 | 3/2011 | Haddon et al. |
| 2011/0166563 A1 | 7/2011 | Cheng et al. |
| 2011/0172756 A1 | 7/2011 | Doerr et al. |
| 2011/0223255 A1 | 9/2011 | Theisen et al. |
| 2011/0275980 A1 | 11/2011 | Weber et al. |
| 2012/0034707 A1 | 2/2012 | Datta et al. |
| 2012/0095461 A1 | 4/2012 | Herscher et al. |
| 2012/0190911 A1 | 7/2012 | McKenna et al. |
| 2012/0193099 A1 | 8/2012 | Vinegar et al. |
| 2012/0296326 A1 | 11/2012 | Manwaring et al. |
| 2013/0012934 A1 | 1/2013 | Manwaring et al. |
| 2013/0026978 A1 | 1/2013 | Cooley et al. |
| 2013/0165916 A1* | 6/2013 | Mathur ................. A61B 18/18 606/33 |
| 2013/0165917 A1 | 6/2013 | Mathur et al. |
| 2013/0197614 A1 | 8/2013 | Gustus et al. |
| 2013/0245357 A1 | 9/2013 | Chauhan et al. |
| 2013/0338571 A1 | 12/2013 | Chambers |
| 2014/0056982 A1 | 2/2014 | Andersen |

FOREIGN PATENT DOCUMENTS

| | | |
|---|---|---|
| WO | 9732532 A1 | 9/1997 |
| WO | 02089863 A1 | 11/2002 |
| WO | 2003051450 A1 | 6/2003 |
| WO | 2005084645 A1 | 9/2005 |
| WO | 2006023261 A2 | 3/2006 |
| WO | 2006125452 A1 | 11/2006 |
| WO | 2006023261 A3 | 4/2009 |
| WO | 2012078745 A1 | 6/2012 |
| WO | 2013096919 A1 | 6/2013 |
| WO | 2013167147 A1 | 11/2013 |

OTHER PUBLICATIONS

Shimizu et al. "Ferromagnetic Exchange Interaction and Curie Temperature of Mg1=xFe2—2xTixO4 (x=0.05) System," J. Magn. Magn. Mater., 310: 1835-1837, 2007.
"Curie temperature", Wikipedia.com, Downloaded Sep. 24, 2013, http://en.wikipedia.org/wiki/Curie_temperature.
"Fluid Bed Coating", Glatt, Downloaded Nov. 4, 2013, http://www.glatt.com/cm/en/process-technologies/coating/fluid-bed-c.

(56) References Cited

OTHER PUBLICATIONS

"Metcal, the original SmartHeat Soldering inventor", YouTube.com, 2011 https://www.youtube.com/watch?v=S9Wmqc9O24w.
"Parylene", Wikipedia.com, Last Modified Oct. 7, 2014, https://en.wikipedia.org/wiki/Parylene.
"Tiny bottles and melting corks: Temperature regulates new delivery system for drugs and fragrances", Phys.org, 2013 http://phys.org/news/2013-09-tiny-bottles-corks-temperature-delivery.html.
"Ultrasonic Dispersing and Deagglomeration", hielscher.com, http://www.hielscher.com/disperse.htm?gclid=CN2x15iQy7oCFXC . . . 2013.
"What is SmartHeat", OkInternational, 2013 http://www.okinternational.com/metcal/english/globalnavigation/appl . . . .
Androlowics et al., "Hyperthermic Ablation of Hepatic Tumors by Inductive Heating of Ferromagnetic Alloy Implants", 2003, http://ecommons.cornell.edu/bitstream/handle/1813/126/Ablation.pdf; isessionid=05E54F77B51462AE4A28301B41A1D549?sequence=2.
Atsarkin et al., "Solution to the bioheat equation for hyperthermia with La1—xAgyMnO3-d nanoparticles: The effect of temperature autostabilization", International Journal of Hypothermia, 25(3): 240-247, 2009.
Berkman et al., "The Effect of Mn Concentration on Curie Temperature and Magnetic Behavior of MOCVD Grown GaMnN Films", Researchgate.com, pp. 834, 2003, http://www.researchgate.net/publication/232027799_The_Effect_of_Mn_Concentration_on_Curie_Temperature_and_Magnetic_Behavior_of_MOCVD_Grown_GaMnN_Films.
Bao et al., "Fabrication and characterization of porous poly(lactic-co-glycolic acid) (PLGA) microspheres for use as a drug delivery" J Mater Sci, vol. 46, pp. 2510-2517, 2011.
Caldwell., "Heat Therapy Could Be New Treatment for Parasitic Skin Disease", Research Communications, 2011, http://researchnews.osu.edu/archive/healtherapy.htm.
Deepayan., "Novel Diluted Magnetic Semiconductor Materials Based on Zinc Oxide", UMI, 2008, https://books.google.com/books?id=ZUu6xrMnmLUC&lpg=PA11&ots=ccAe7eYc2h&dq=%22Curie+temperature%22+%22zinc+oxide%22&pg=PA19&hl=en#v=onepage&q&f=false.
Gomez-Polo et al., "Analysis of heating effects (magnetic hyperthermia) in FeCrSiBCuNb amorphous and nanocrystalline wires", Journal of Applied Physics III, pp. 07A314(1-3), 2012.
Habib et al., "Evaluation of iron-cobalt/ferrite core-shell nanoparticles for cancer thermotherapy", Journal of Applied Physics, vol. 103, Issue 7, pp. 07A307(3 pages), 2008.
Jiang et al., "A micro heater platform with fluid channels for testing micro-solid oxide fuel cell components" Sensors and Actuators B: Chemical, vol. 175, pp. 218-224, 2012, http://www.ltnt.ethz.ch/publications/Journal/pubimg/2012_Jiang1.pdf.
Jiang et al., "Elsevier Editorial System(tm) for Sensors & Actuators: B. Chemical Manuscript Draft", Eurosensors, SNB-D-11-01569R1, 2011, http://infoscience.epfl.ch/record/182711/files/2012%20Jiang%20SNB%20-%20plateforme%20chauffante%20verre%20AF32%20-%20preprint.pdf.
Litton et al., "Zinc Oxide Materials for Electronic and Optoelectronic Device Applications", John Wiley & Sons, 2011, https://books.google.com/books?id=_QGfgEmuVF8C&dq=%22Curie+temperature%22+%22zinc+oxide%22&source=gbs_navlinks_s.
Liu et al., "Ferromagnetism of ZnO and GaN: A Review", Journals of Material Science: Materials in Electronics, 16(9): 555-597, 2005 http://link.springer.com/article/10.1007/s10854-005-3232-1.
Martirosyan., "Thermosensitive Magnetic Nanoparticles for Self-Controlled Hyperthermia Cancer Treatment", Nanomedicine and Nanotechnology, 3(6): 2 pages, 2012.
McNerny et al., "Chemical synthesis of monodisperse y-Fe—Ni magnetic nanoparticles with tunable Curie temperatures for self-regulated hyperthermia", Journal of Applied Physics, vol. 107, pp. 09A312(1-3), 2010.

Mendelsohn, "Does Complete Renal Denervation Translate into Superior Clinical Outcomes? Lessons Learned from Denervation of Accessory Renal Arteries", Clinical Research in Cardiology, 103(9):681-683, Mar. 26, 2014.
Miller et al., "Fe—Co—Cr nanocomposites for application in self-regulated rf heating", Journal of Applied Physics, vol. 107, pp. 09A313(1-3), 2010.
Pana et al., "Synthesis and characterization of LSMO nanoparticles covered with Au having a core-shell structure", Journal of Physics: Conference Series, vol. 182, 2009.
Pearton et al., "Room temperature ferromagnetism in GaMnN and GaMnP" Physica status solidi 195(1):222-227, 2003 http://onlinelibrary.wiley.com/doi/10.1002/pssa.200306283/abstract.
Pham et al., "A simple approach for immobilization of gold nanoparticles on graphene oxide sheets by covalent bonding", Applied Surface Science, vol. 257, pp. 3350-3357, 2011.
Rehman et al. "Ferromagnetic self-regulating reheatable thermal rod implants for in situ tissue ablation" PubMed.gov, 16(7):523-531, 2002.
Riemer. "Ultrasonic spray coating of nanoparticles", Global Solar Technology, pp. 26-28, 2011 www.globalsolartechnology.com.
Shahil et al. "Graphene-Based Nanocomposites as Highly Efficient Thermal Interface Materials", Graphene Based Thermal Interface Materials, 2011.
Shahil et al. "Thermal properties of graphene and multilayer graphene: Applications in thermal interface materials", Solid StateCommunications, vol. 152, pp. 1331-1340, 2012.
Singer. "Interventional Electrophysiology" 122, 2001 https://books.google.com/books?id=8Gs1O6pG_dYC&pg=PA122&lpg=PA122&dq=curie+temperature+ablation&source=bl&ots=Y9E36OqphP&sig=3SkKSTsPSkwWDLzUe5I2NAljEL0&hl=en&sa=X&ei=3GICUrn1N8msqgGOhYC4Bw#v=onepage&q=curie%20temperature%20ablation&f=false.
Singh et al. "Polymer-Graphene Nanocomposites: Preparation, Characterization, Properties, and Applications", Nanocomposites—New Trends and Developments 37-71, 2012 http://dx.doi.org/10.5772/50408.
Skomski et al. "Curie temperature of multiphase nanostructures", Journal of Applied Physics 87: 9 , 4756-4758, 2000.
Sperling et al. "Surface modification, functionalization and bioconjugation of colloidal inorganic nanoparticles", Philisophical Transactions of the Royal Society 368:1333-1383, 2010.
Theodoropoulou et al. "Magnetic and structural properties of Mn-implanted GaN", Applied Physics Letters 78: 22, 3475-3477, 2001 http://www.researchgate.net/profile/Suhk_Oh/publication/3435502_Magnetic_and_structural_properties_of_Co_ion-implanted_GaN/links/09e4150f351a3305f3000000.pdf.
Wang et al. "Reversible room-temperature magnetocaloric effect with large temperature span in antiperovskite compounds Ga1—xCMn3+x,,x=0, 0.06, 0.07, and 0.08)", Journal of Applied Physics 105: 083907(1-5), 2009.
Wang et al. "Graphene-Based Nanocomposites", InTech, 135-168, Apr. 19, 2011 www.intechopen.com.
Cram et al. "Biomedical Application of Induction Heating: A Novel for Benign Hyperplasia (BPH) Treatment", Jan. 5, 2010 (Jan. 5, 2010), XP055199044, Retrieved from the internet: http://www.uvm.edu/~ugrsrch/posters06/cram_willey.pdf [retrieved on Jun. 30, 2015].
Ahmad et al. "Optimszation of (Gd)5Si4 Based Materials: A Step Towards Self-controlled Hyperthermia Applications," J. Appl. Phys., 106, pp. 064701, 2009.
Akin et al. "Ni1-xCrx Alloy for Self Controlled Magnetic Hyperthermia," Crystal research and Technology, 44(4): 386-390, 2009.
Bose et al. "Exchange Interactions and Curie Temperatures in Cr-based Alloys in Zinc Blende Structure: Volume-and-composition-dependence," arXiv:9012.1760 [condmat.mtrl-sci], 16 pgs, Feb. 5, 2010.
Giri et al. :Investigation on Tc Turned Nano Particles of Magnetic Oxides for Hyperthermia Applications, Biomed. Mater. Eng., 13(4): 387-399, 2003.
Iorga et al. "Low Curie Temperature in Fe—Cr—No—Mn Alloys," U.P.B. Sci. Bull. Series B, 73(4): 195-202, 2011.
Joshi et al. "Role of Biodegradeable Polymers in Drug Delivery," Int. J. Current Pharm. Res., 4(4): 74-81, 2012.

(56) References Cited

OTHER PUBLICATIONS

Kuznetsov et al. "Local Radiofrequency-induced Hyperthermia using CuNi Nanoparticles with Therapeudically Suitable Curie Tempertaure," J. Magn. Magn. Mater., 311: 197-203, 2007.

Martirosyan, "Thermosensitive Magnetic Nanoparticles for Self-Controlled Hyperthermia Cancer Treatment," J. Nanomed. Nanotechol., 3(6): 100e112 (1-2), 2012.

Prasad et al. "TC-Tuned Biocompatible Suspension of La0.73SR0.27MnO3 for Magnetic Hyperthermia," J. Biomed. Mater. Res. B Appl. Biomater., 85:409-416, 2008.

Prasad et al. "Gd Substituted NiCa Ferrite/Poly Vinyl Alchohol Nanocomposite," J. Magn. Magn. Mater., 324: 896-872, 2012.

"Fluidized Bed Spray Coating", Glatt.com, http://www.glatt.com/en/processes/coating/fluidized-bed-coating/, © 2016 copyright 2004-2013.

"Ultrasonic Dispersion Syringe Pump", SonoTek, http://www.sono-tek.com/sonicsyringe/, © 2015.

Mendelsohn, "Does complete renal denervation translate into superior clinical outcomes? Lessons learned from denervation of accessory renal arteries", Clin Res Cardiol, 103:681-683, 2014.

\* cited by examiner

DEVICES AND METHODS FOR THERAPEUTIC HEAT TREATMENT

CROSS-REFERENCE TO RELATED APPLICATIONS

The following commonly assigned patent applications are incorporated herein by reference, each in its entirety:

U.S. Pat. App. Ser. No. 61/980,995 (Sutermeister et al.), entitled DEVICES AND METHODS FOR THERAPEUTIC HEAT TREATMENT, filed on Apr. 17, 2104.

U.S. Pat. App. Ser. No. 61/980,952 (Sutermeister et al.), entitled MEDICAL DEVICES FOR THERAPEUTIC HEAT TREATMENTS, filed on Apr. 17, 2014; and U.S. Pat. App. Ser. No. 61/981,003 (Sutermeister et al.), entitled COMPOSITIONS FOR THERAPEUTIC HEAT DELIVERY, filed on Apr. 17, 2014 and U.S. Pat. App. Ser. No. 61/980,936 (Sutermeister et al.), entitled DEVICES AND METHODS FOR THERAPEUTIC HEAT TREATMENT, filed on Apr. 17, 2104.

TECHNICAL FIELD

The present disclosure pertains to medical devices, systems, and methods for delivery of heat (e.g., therapeutic treatment using heat). In one or more embodiments, the present disclosure pertains to heat treatment for medical applications (e.g., nerve modulation or ablation, etc.).

BACKGROUND

Certain treatment procedures include temporary or permanent modulation (e.g., interruption, modification, stimulation, ablation, denervation, etc.) of one or more select nerve functions. One example, among many, is renal nerve ablation, which is sometimes used to treat conditions related to, for example, hypertension and congestive heart failure. In some instances, other disorders such as COPD (chronic obstructive pulmonary disease such as chronic bronchitis) can be treated by nerve modulation.

For renal nerve ablation, a balloon catheter may be used to ablate target nerves. For example, balloons have included electronic circuits (e.g., flex circuits, etc.) attached to the balloon's outer surface with one or more pairs of electrodes connected to an internal or external power supply to deliver RF (i.e., radio frequency) energy to a target nerve. In some cases, the balloon has included temperature sensors (e.g., thermocouples, thermistors, etc.) for monitoring temperature and for feedback control to sufficiently heat the target nerves without undue overheating and consequential undue damage to surrounding tissue. In many cases, multiple heating elements and temperature sensors have made the electronic circuits complicated and have also increased the overall profile of the system. However, reducing profile of medical devices (e.g., balloon catheters, etc.) and reducing circuitry complication are ongoing needs.

Hence, there exists a need to develop robust devices and methods to deliver heat (e.g., therapeutic heat treatment, etc.) for nerve modulation with temperature control using less complicated electronic circuitry and/or with a reduced profile.

SUMMARY

In one or more embodiments, a medical device for nerve modulation includes an expandable medical device, such as a balloon catheter, and at least one thermistor array.

In one more embodiments, a medical device for nerve modulation includes an elongate shaft having a proximal end region and a distal end region. An expandable device may be positioned adjacent to the distal end region of the elongate shaft. At least one thermistor array may disposed on an outer surface of the expandable device, the at least one thermistor array comprising at least two thermistors and being operatively engaged with a source of electric current, each of the at least two thermistors having a resistance that varies with temperature In one or more embodiments a balloon catheter includes a balloon structured and arranged to be disposed within a vessel that defines a vessel lumen. The balloon includes a balloon wall. In one or more embodiments, the thermistor array is disposed on the balloon wall, includes at least two thermistors, and is operatively engaged with a source of electric current. Each of the at least two thermistors has a resistance that varies with temperature. In one or more embodiments, the medical device is configured and arranged to transfer heat to the medical device surroundings, wherein at least 50 percent of the heat transferred from the medical device to the medical device surroundings is generated by resistance heating (i.e., Joule heating).

In one or more embodiments, a method of nerve modulation is disclosed. The method includes receiving a medical device that includes at least one thermistor (e.g., thermistor array), disposing at least one thermistor (e.g., thermistor array) proximate a nerve to be modulated, and transferring heat from the medical device to the nerve to modulate the nerve, wherein at least 50 percent of the heat transferred from the medical device is generated by resistance heating. In one or more embodiments, the medical device includes a balloon catheter and the at least one thermistor (e.g., thermistor array). The balloon catheter includes a balloon structured and arranged to be disposed within a vessel that defines a vessel lumen. The balloon includes a balloon wall with the at least one thermistor (e.g., thermistor array) disposed on the balloon wall. In one or more embodiments including at least one thermistor array, the at least one thermistor array includes at least two thermistors and is operatively engaged with a source of electric current. Each of the at least two thermistors has a resistance that varies with temperature.

In one or more embodiments, a device (e.g., for nerve modulation) is disclosed. The device may include an expandable balloon including an outer surface and defining a balloon longitudinal axis extending from a proximal end to a distal end of the expandable balloon. The device may also include at least one flexible circuit mounted on the outer surface of the expandable balloon. In one or more embodiments, the at least one flexible circuit includes a first insulating layer, a second insulating layer above the conductive layer, and a conductive layer between the first insulating layer and the second insulating layer, at least one temperature-sensing device that includes at least one thermistor, wherein at least a portion of the conductive layer is electronically coupled to the thermistor, with the proviso that no electrode is associated with the conductive layer.

In one or more embodiments, a medical device is disclosed, the medical device including a balloon and a thermistor disposed on the balloon. In some embodiments, the thermistor is configured and arranged to increase in temperature (e.g., via resistive heating) to a treatment temperature (e.g., at least 30° C.), upon delivery of an electric current thereto, and a temperature of the thermistor may be determined via a determination of an electrical resistance (e.g., using an ohmmeter) of the thermistor.

The above summary of one or more embodiments is not intended to describe every disclosed embodiment or every implementation of the subject matter of the present disclosure. The drawings and detailed description, which follow, more particularly describe one or more embodiments of the present disclosure.

BRIEF DESCRIPTION OF THE DRAWINGS

A detailed description is hereafter provided with specific reference being made to the drawings.

Figure 1A:
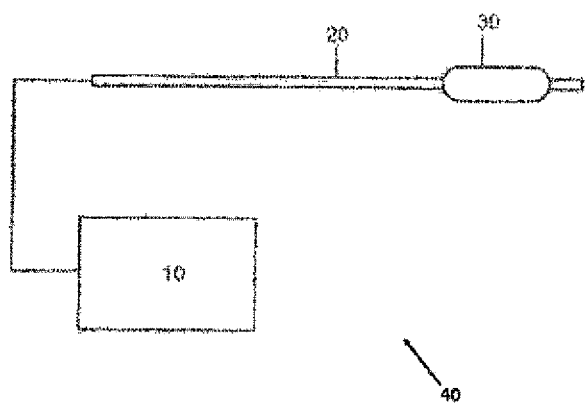
FIG. 1A shows a simplified schematic of a system for remodeling tissue according to one or more embodiments of the present disclosure.

While the disclosure is amenable to various modifications and alternative forms, specifics thereof are shown by way of example in the drawings and are described in detail. It should be understood, however, that the intention is not to limit the present disclosure to the particular embodiments described. On the contrary, the intention is to cover all modifications, equivalents, and alternatives falling within the scope of the present disclosure.

DETAILED DESCRIPTION

Definitions are provided for the following defined terms. It is intended that these definitions be applied, unless the context indicates otherwise.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the term "about" may include numbers that are rounded to the nearest significant figure.

The recitation or disclosure of numerical ranges by endpoints includes all numbers within that range (e.g., 1 to 5 includes 1, 1.5, 2, 2.75, 3, 3.80, 4, and 5).

As used herein, the singular forms "a", "an", and "the" include plural references unless the context clearly indicates otherwise. As used herein, the term "or" is generally employed in its sense including "and/or" unless the content clearly indicates otherwise.

References herein to "one or more embodiments," "an embodiment," "some embodiments," etc., indicate that the embodiment described may include a particular feature, structure, or characteristic, but not every embodiment necessarily includes the particular feature, structure, or characteristic. Moreover, such phrases do not necessarily refer to the same embodiment. Further, when a particular feature, structure, or characteristic is described in connection with one embodiment (or more embodiments), it should be understood that such feature, structure, or characteristic may also be used in connection with other embodiments, whether or not explicitly described, unless clearly stated to the contrary.

It should be noted that references herein to the term "distal" are to a direction away from an operator, while references to the term "proximal" are to a direction towards the operator. Accordingly, when the terms "distal" and "proximal" are used herein in the context of an apparatus that is being deployed within a body, such as a human body, by an operator, the term "distal" refers to a location within the body that is farther within the body than a location that is "proximal" to the operator.

"Thermistor" is a resistor whose electrical resistance varies drastically with changes in temperature. Thus, thermistor is commonly used for sensing sensitive temperature changes.

"Curie temperature" is defined as the temperature at which permanent magnetic properties of a material convert into induced magnetic properties, or vice versa.

"Curie materials" refer to those metals or metal alloys that exhibit magnetic properties based on selected Curie temperatures. The Curie temperature of a Curie material may be altered by using composite materials, which may or may not be ferromagnetic. Changes in doping, additives, composites, alloying, and density of Curie materials can alter the structure and behavior of the Curie material and the Curie temperature.

Various procedures, such as renal nerve ablation, may require delivery of heat for ablating nerves to treat conditions related to hypertension and/or congestive heart failure. The kidneys produce a sympathetic response to congestive heart failure, which, among other effects, increases the undesired retention of salts and/or water. Ablating at least some of the nerves running to the kidneys may reduce this sympathetic response, reducing associated undesired symptoms.

Many nerves (and nervous tissue, such as brain tissue), including renal nerves, run along the walls of, or in close proximity to, blood vessels, and thus can be accessed intravascularly i.e., through patient's blood vessels. In one or more embodiments, energy (e.g., thermal, ultrasonic, laser, microwave, RF energy, etc.) may be applied to the wall of the blood vessel.

In other example, energy may be applied to walls of airways of a patient to treat symptoms of respiratory disorders such as COPD (e.g., chronic bronchitis). Medical devices such as ablation catheters (or balloon catheters) are commonly used for application of the energy.

Certain treatments are aimed at the temporary or permanent interruption or modification of select nerve function. In some embodiments, the nerves may be sympathetic nerves. One example treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating at least some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure).

Some embodiments of the present disclosure include a power generating and control apparatus, often for the treatment of targeted tissue in order to achieve a therapeutic effect. In some embodiments, the target tissue is tissue containing or proximate to nerves. In other embodiments, the target tissue is sympathetic nerves, including, for example, sympathetic nerves disposed adjacent to blood vessels. In still other embodiments the target tissue is luminal tissue, which may further comprise diseased tissue such as that found in arterial disease.

In some embodiments of the present disclosure, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to the vessel wall, neighboring nerves, and organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need to be in exact contact, as would be required when using a typical ablation probe. For example, eccentric heating may be applied at a temperature high enough to denature nerve tissue without causing ablation and without requiring the piercing of luminal tissue. However, it may also be desirable to configure the energy delivery surface of the present disclosure to pierce tissue and deliver ablating energy similar to an ablation probe with the exact energy dosage being controlled by a power control and generation apparatus.

In some embodiments, efficacy of the denervation treatment can be assessed by measurement before, during, and/or after the treatment to tailor one or more parameters of the treatment to the particular patient or to identify the need for additional treatments. For instance, a denervation system may include functionality for assessing whether a treatment has caused or is causing a reduction in neural activity in a target or proximate tissue, which may provide feedback for adjusting parameters of the treatment or indicate the necessity for additional treatments.

Many of the devices and methods described herein are discussed relative to renal nerve ablation and/or modulation. However, it is contemplated that the devices and methods may be used in other treatment locations and/or applications where sympathetic nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pain management, pulmonary vein isolation, pulmonary vein ablation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue.

The following detailed description should be read with reference to the drawings in which similar elements in different drawings are numbered the same. The drawings, which are not necessarily to scale, depict illustrative embodiments and are not intended to limit the scope of the disclosure.

In one or more aspects of the present disclosure, a medical device for nerve modulation includes a balloon catheter and at least one thermistor array, wherein the medical device is configured and arranged to transfer heat to the medical device surroundings and wherein at least 50 percent of the heat transferred from the medical device to the medical device surroundings is generated by resistance heating. The balloon catheter includes a balloon that includes a balloon wall and is structured and arranged to be disposed within a vessel (e.g., a blood vessel, etc.) that defines a vessel lumen (e.g., a body lumen, etc.).

In one or more embodiments, at least one thermistor array is disposed on the balloon wall. In the present disclosure, a "thermistor array" refers to at least two thermistors that are arranged along a line when the surface on which the thermistors are disposed is flat. That is, in embodiments in which a thermistor array is disposed on the surface of a cylindrical balloon, the thermistors of the thermistor array will be arranged along a line when the balloon is made flat.

In one or more embodiments, the line along which two or more thermistors are arranged in a thermistor array includes a straight line extending parallel to an axis of a balloon (e.g., extending longitudinally along the surface of a balloon), or a straight line extending laterally around a balloon (e.g., extending circumferentially once around a balloon, represented by a circular or elliptical shape when the balloon is expanded), or a straight line extending in a direction not parallel to the longitudinal axis of the balloon nor at a right angle thereto (e.g., extending helically around and longitudinally along a balloon when the balloon is expanded, as a helix). In one or more embodiments, the line along which two or more thermistors are arranged in a thermistor array passes through the geometric center of each thermistor of the thermistor array. In one or more embodiments, a plurality of thermistors form a pattern (e.g., a two-dimensional pattern) having a plurality of intersecting thermistor arrays. In some embodiments, the thermistors may be arranged on a square or rectangular grid.

In one or more embodiments, the at least one thermistor array may include at least a first plurality of thermistors, wherein each of the first plurality of thermistors is disposed at a first longitudinal distance from a proximal end of the balloon. This is the case wherein a thermistor array includes at least two thermistors arranged along a straight line extending laterally around a balloon (e.g., extending circumferentially once around a balloon, represented by a circular or elliptical shape when the balloon is expanded). In one or more embodiments, the thermistor array includes at least a second plurality of thermistors, wherein each of the second plurality of thermistors is disposed at a second longitudinal distance from the proximal end of the balloon.

In one or more embodiments, the at least two thermistors of a thermistor array may be evenly distributed (e.g., spaced) along the line. That is, if a thermistor array extends in a direction around the circumference of a balloon, the thermistors may, in some embodiments, be 180 degrees apart, 120 degrees apart, 90 degrees apart, 72 degrees apart, 60 degrees apart, etc. In other embodiments, the thermistors are not evenly distributed along a line.

In one or more aspects of the present disclosure, a medical device (e.g., for nerve modulation, etc.) includes a balloon and a thermistor disposed on the balloon. In some embodiments, the thermistor is configured and arranged to increase in temperature to a treatment temperature (e.g., at least 30° C., etc.), upon delivery of an electric current thereto. In one or more embodiments, the increase in temperature is due primarily to resistive heating (i.e., Joule heating) of the thermistor. In one or more embodiments, a temperature of the thermistor may be determined via a determination of an electrical resistance of the thermistor.

In the present disclosure, thermistors are operatively engaged with a source of electric current and have a resistance that varies with temperature. In one or more embodiments, a medical device includes a source of electric current electrically coupled to the thermistor (e.g., in an electric circuit that includes one or more conductive traces, etc.) and includes a resistance-determining device (e.g., an ohmmeter, etc.) configured to determine the resistance of the thermistor. In one or more embodiments, the electric resistance of the thermistor is converted to temperature based on a predetermined relationship between the temperature and electric resistance of the thermistor. The predetermined relationship between the thermistor's temperature and electric resistance may be based on, for example, results of calibrating a thermistor and/or a theoretical correlation between temperature and resistance based on a thermistor's chemical and physical characteristics (e.g., composition, dimensions, etc.), with appropriate adjustments made for electric resistance of other components in the electric circuit with the thermistor.

In one or more embodiments, a thermistor (e.g., thermistor array) operatively engaged with a source of electric current includes a first conductive trace (e.g., a wire, etc.) extending from the source of electric current to the at least one thermistor (e.g., thermistor array) and a second conductive trace (e.g., a wire, etc.) extending from the at least one thermistor (e.g., thermistor array) to a ground, which may be a shared or common ground associated with two or more thermistors of a thermistor array or which may be one or multiple grounds in an embodiment in which each of at least two thermistors is associated with (e.g., has) an independent ground. In one or more embodiments, a thermistor (e.g., thermistor array) may be associated with an independent ground relative to one or more other thermistors (e.g., thermistor arrays).

In one or more embodiments, a source of electric current may include, but is not limited to radio frequency (RF), alternating current (AC), and/or direct current (DC).

In one or more embodiments, the medical device provides heat to its surroundings, which may include a lumen wall (e.g., biological tissue, etc.). In one or more embodiments, at least 50 percent of the heat transferred from the medical device to the medical device surroundings is generated by resistance heating of one or more thermistors. In some embodiments, even more than 50 percent (e.g., at least 60 percent, at least 75 percent, at least 90 percent, at least 95 percent, at least 99 percent, etc.) of heat transferred from the medical device is generated by resistance heating of one or more thermistors. In one or more embodiments, all or substantially all of the heat transferred from the medical device to the medical device surroundings is generated by resistance heating of one or more thermistors.

As further described herein, in one or more embodiments, a thermistor array may include at least three thermistors. In some embodiments, a thermistor array includes more than three (e.g., at least 4, at least 5, at least 6, etc.) thermistors.

In another aspect of the present disclosure, a device includes an expandable balloon, a flexible circuit that includes among other things, a conductive layer electrically coupled to a thermistor, wherein no electrode is associated with the conductive layer. The expandable balloon includes an outer surface and defines a balloon longitudinal axis extending from a proximal end to a distal end of the expandable balloon. In one or more embodiments, the at least one flexible circuit is mounted on the outer surface of the expandable balloon. As further described herein the at least one flexible circuit can include a first insulating layer, a second insulating layer above the conductive layer, and a conductive layer between the first insulating layer and the second insulating layer. The flexible circuit also includes at least one temperature-sensing device that includes at least one thermistor, wherein at least a portion of the conductive layer is electronically coupled to the thermistor and with the proviso that no electrode is associated with the conductive layer. Although no electrode is associated with the conductive layer that is electrically coupled with the thermistor, the medical device may, in one or more embodiments, include one or more electrodes, such as those described by Mathur et al. (WO 2013/096919 A1) the full disclosure of which is incorporated herein by reference.

In one or more embodiments, the at least one thermistor is positioned at least partially within the first insulating layer. For example, the first insulating layer may include one or more apertures extending therethrough that allow the placement of a thermistor at least partially therein. In this way, a thermistor may be electrically coupled to the conductive layer, in at least some embodiments.

In one or more embodiments, the at least one thermistor has a thickness of less than approximately 0.15 millimeters (mm). In one or more embodiments, the at least one thermistor may include (1) an alumina base having a length of about 0.95 mm to about 1.15 mm (e.g., 1.05 mm) and a width of about 0.45 mm to about 0.65 mm (e.g., 0.55 mm), and a thickness of about 0.07 to about 0.13 mm (e.g., 0.10 mm); (2) a glass thermistor having a length of about 0.43 mm and a width of about 0.46 to about 0.50 mm (e.g., 0.48 mm) centered on the alumina base; and (3) two gold plates disposed on the alumina base next to the glass thermistor and having a length of about 0.26 to about 0.30 mm (e.g., 0.28 mm) and a width of about 0.46 to about 0.50 mm (e.g., 0.48 mm) and a thickness less than 0.015 mm. In one or more embodiments, the length of a thermistor may be in a range of from about 2 millimeters (mm) to about 6 mm. In one or more embodiments, the width of a thermistor may be in a range of from about 200 micrometers to about 1 millimeter.

In one or more embodiments, the thermistor may include any of a wide variety of materials of construction including, but not limited to, one or more metal oxides of manganese, nickel, cobalt, copper, aluminum, and iron. In one or more embodiments, an NTC-type thermistor may be formed as an n-type semiconductor using materials such as ferric oxide ($Fe_2O_3$) with titanium (Ti) doping, wherein the charge carriers are electrons. In one or more embodiments, an NTC-type thermistor may be formed as a p-type semiconductor using materials such as nickel oxide (NiO) with lithium (Li) doping, wherein the charge carriers are holes. In some embodiments, a PTC-type thermistor may be formed from a doped polycrystalline ceramic containing barium titanate ($BaTiO_3$) and other compounds, which may also serve as a radiopaque marker in some applications. The dielectric constant of this ferroelectric material varies with temperature. Below the Curie temperature, the high dielectric constant may prevent the formation of potential barriers between the crystal grains, leading to a low resistance. In this region, the device has a small negative temperature coefficient. At the Curie temperature, the dielectric constant drops sufficiently to allow the formation of potential barriers at the grain boundaries, and the resistance increases sharply. At even higher temperatures, the material reverts to NTC behavior.

In one or more embodiments, the thermistor may include a silistor, a thermally sensitive silicon resistor. A silistor may employ silicon as the semiconductive component material. In contrast to the switching-type thermistor, silistors have an almost linear resistance-temperature characteristic.

In one or more embodiments, a material having increased thermal conductivity relative to the second insulating layer is positioned at least partially within the second insulating layer and is in contact with the at least one thermistor. For example, the second insulating layer may include one or more apertures in which a material having enhanced thermal conductivity may be placed. In this manner, heat generated by the resistive heating of the thermistor may be more efficiently transferred to the medical device surroundings. In one or more embodiments, the at least one temperature-sensing device is structured and arranged to measure a temperature representative of an outer surface of at least a portion of the flexible circuit. In one or more embodiments, measuring the resistance of the thermistor may allow conversion to a temperature of the thermistor itself. In some embodiments, determination of the thermistor temperature may allow for the determination of the temperature of, for example, an outer surface of at least a portion of the flexible circuit when the thermal conductivities and dimensions of such materials are known.

As further discussed herein, in one or more embodiments, the at least one flexible circuit may include at least a plurality of thermistors that are arranged along a first longitudinal axis approximately parallel to the balloon longitudinal axis.

FIG. 1A shows a system 40 for performing a treatment within a body passageway. The system 40 includes a control unit 10. The control unit 10 can include an energy generator (e.g., an RF generator, etc.) for delivering energy (e.g., RF energy) to catheter device 20. An exemplary control unit and associated energy delivery methods useable with the embodiments disclosed herein are disclosed in commonly assigned U.S. Pat. App. Pub. No. US 2012/0095461, which is incorporated by reference herein. Further examples useable with the embodiments disclosed herein are disclosed in commonly assigned U.S. Pat. No. 7,742,795 entitled "Tuned RF Energy for Selective Treatment of Atheroma and Other Target Tissues and/or Structures", U.S. Pat. No. 7,291,146 entitled "Selectable Eccentric Remodeling and/or Ablation of Atherosclerotic Material", and U.S. Pub. No. 2008/0188912 entitled "System for Inducing Desirable Temperature Effects on Body Tissue," the full disclosures of which are incorporated herein by reference.

Returning to FIG. 1A, the catheter device 20 can include an expandable device 30, which can be a compliant, non-compliant, or semi-compliant balloon, an expandable basket, or expandable stent-like structure. It is further contemplated that, while not explicitly shown, the catheter device 20 may also include other structures, such as a deflectable tip or a coiled structure that may be used to bring a flexible circuit into contact with or close proximity to a desired treatment region. As further described herein, the expandable device 30 includes at least one thermistor (e.g., of a thermistor assembly, of a thermistor array, etc.) electrically coupled to the control unit 10. Such thermistors can be electrically configured to have temperature sensing capability.

Figure 1B:
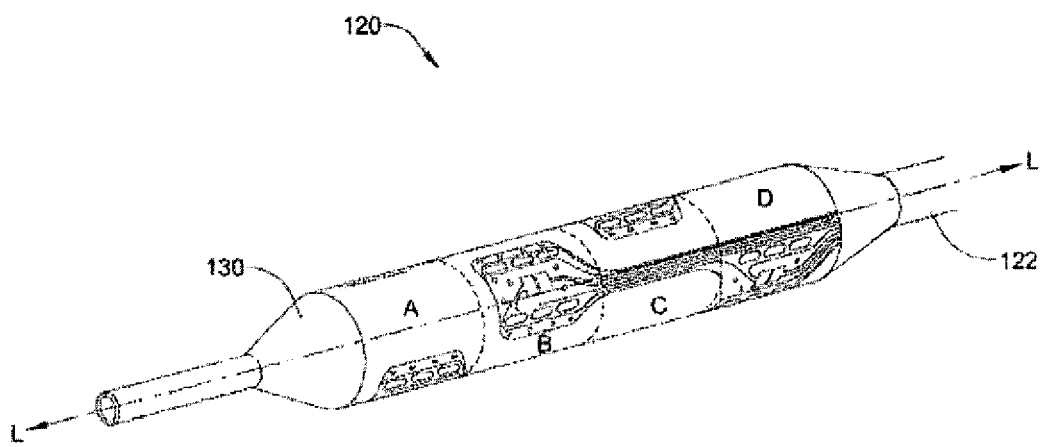
FIG. 1B is a perspective view of a prior art expandable device of a catheter.

As shown in FIG. 1B (prior art), electrode assemblies have been arranged on an expandable device 130 (similar to expandable device 30) of a catheter device 120, shown here in an expanded state, according to a plurality of cylindrical treatment zones A-D. In one or more embodiments, the expandable device 130 or other components of the system may include electrode assemblies that are not in a treatment zone or are otherwise not used or configured to deliver a treatment energy. The catheter device 120 may include an elongate shaft 122 extending proximally from the expandable device 130.

Figure 1C:
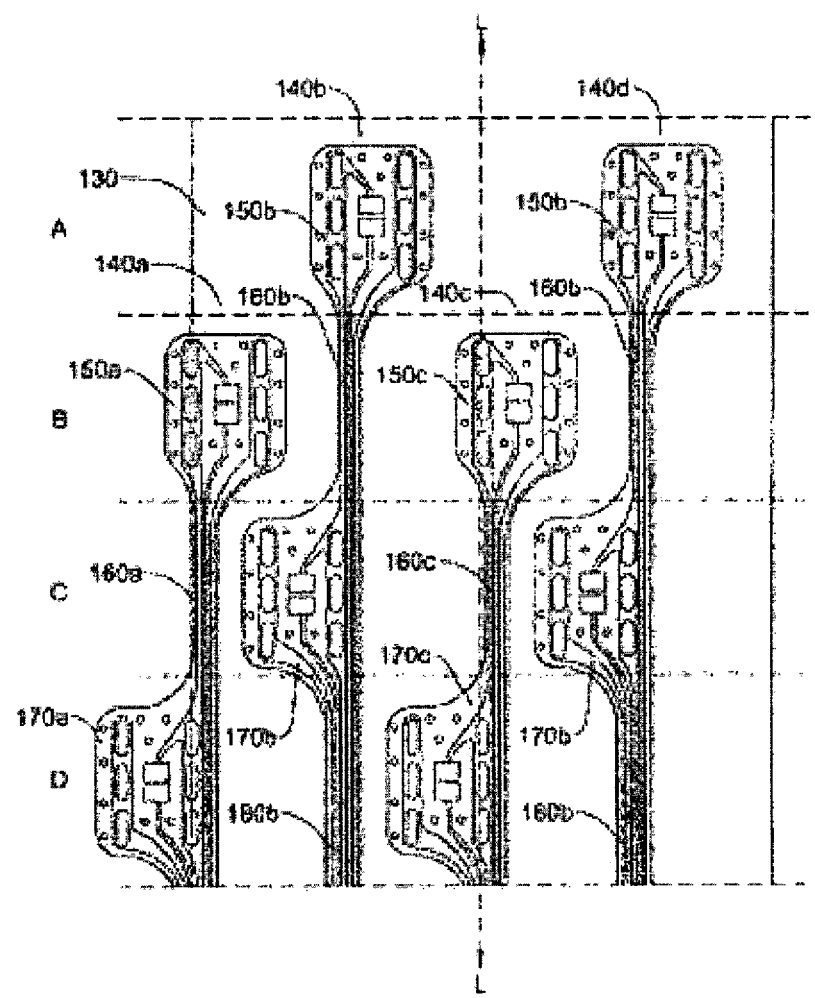
FIG. 1C is a top view of the expandable device of FIG. 1B in an unrolled configuration.

The treatment zones A-D and associated electrode assemblies 140a-d are further illustrated in FIG. 1C (prior art), which is a flat, "unrolled" depiction of the expandable device 130 of FIG. 1B (prior art). In some embodiments, the expandable device 130 has been a balloon with a 4 mm diameter and two electrode assemblies 140a-b. In other embodiments, the expandable device has been a balloon with a 5 mm diameter and three electrode assemblies 140a-c. In some embodiments, the expandable device has been a balloon with a 6, 7, or 8 mm diameter and four electrode assemblies 140a-d, as depicted in FIG. 1B. For any of these configurations, the expandable device 130 might have a working length of about 10 mm to about 100 mm, or about 15 mm to about 32 mm (e.g., about 18 mm to about 25 mm), which is the approximate longitudinal span of all the treatment zones A-D shown in FIGS. 1B and 1C. The electrode assemblies 140a-d have been attached to a balloon using adhesive, or other bonding technique.

In one or more embodiments, a device of the present disclosure may include a first thermistor and a second thermistor separated by a first distance. The first thermistor may be heated by delivery of a current thereto and the second thermistor may be used to measure the temperature at the second thermistor to determine whether the thermal plume extends at least the first distance (i.e., between the first and second thermistors). In one or more embodiments, the second thermistor may be used to determine whether the target temperature zone extends at least the first distance. Thus, in one or more embodiments, a first plurality of thermistors may be used to generate heat and a second plurality of thermistors may be used to measure the extent of target temperature zones and/or thermal plumes.

Returning to FIG. 1C (prior art), each electrode pad assembly 140a-d includes four major components, which are a distal electrode pad 150a-d, intermediate tail 160a-d, proximal electrode pad 170a-d, and proximal tail 180b,d (not shown for electrode pad assemblies 140b and 140c). Constructional details of the electrode assemblies 140a-d are shown and described with reference to FIG. 1D (prior art).

Figure 1D:
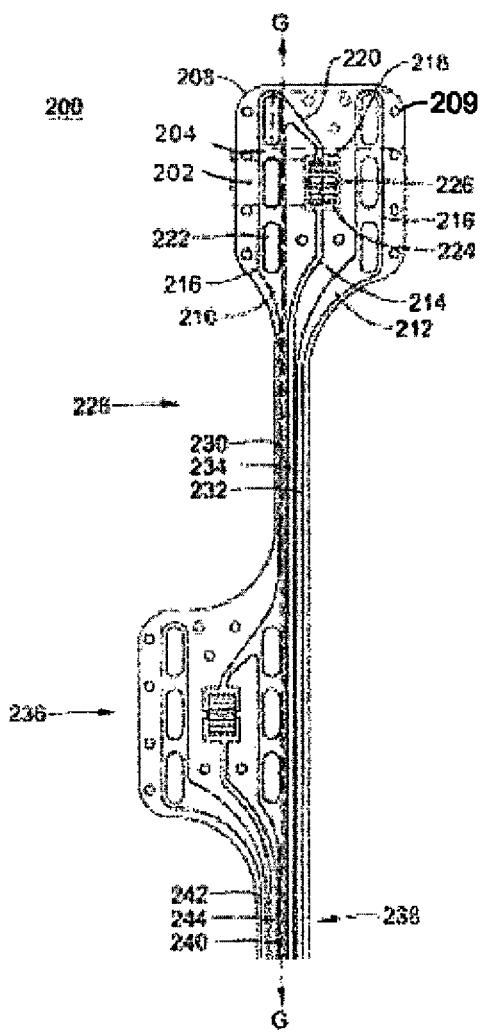
FIG. 1D is a top view of one of the flexible circuits of FIG. 1C including an electrode assembly.

FIG. 1D (prior art) shows a top view of an electrode assembly 200, which is identified in FIG. 1C (prior art) as electrode assemblies 140a-d. The electrode assembly 200 has been constructed as a flexible circuit having a plurality of layers. Such layers can be continuous or noncontiguous, i.e., made up of discrete portions. A base layer 202 of insulation provides a foundation for the electrode assembly 200. The base layer 202 can be constructed from a polymer such as polyimide or a flexible polymer. In some embodiments, the base layer 202 is approximately 0.5 mil (0.0127 mm) thick. A conductive layer 204 made up of a plurality of discrete traces is layered on top of the base layer 202. The conductive layer 204 can be, for example, a layer of electrodeposited copper. In some embodiments, the conductive layer 204 is approximately 0.018 mm thick. An insulating layer (not shown, but could have the same or different shape as base layer 202) is discretely or continuously layered on top of the conductive layer 210, such that the conductive layer 204 is fluidly sealed between the base layer 202 and the insulating layer (not shown). Like the base layer 202, the insulating layer can be constructed from a flexible polymer such as polyimide. In some embodiments, the insulating layer (not shown) is approximately 0.5 mil (0.0127 mm) thick. In other embodiments, the insulating layer (not shown) is a complete or partial polymer coating, such as polytetrafluoroethylene (PTFE) or silicone.

The electrode assembly 200 shown in FIG. 1D includes a distal electrode pad 208. In this region, the base layer 202 at distal electrode pad 208 forms a generally rectangular shape. As shown, the electrode assembly 200 may include a plurality of openings 209 to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail insertion and withdrawal through an insertion sheath or guide), such as may be needed when multiple sites are treated during a procedure.

In FIG. 1D (prior art), the distal electrode pad 208 includes a plurality of discrete traces layered on top of the base layer 202. These traces include a ground trace 210, an active electrode trace 212, and a sensor trace 214. The ground trace 210 includes an elongated electrode support 216 laterally offset from a sensor ground pad 218. The sensor ground pad 218 is electrically coupled to the elongated support 216 of the ground trace 210 and is centrally located on the distal electrode pad 208. A bridge 220 connects a distal most portion of the sensor ground pad 218 to a distal portion of the elongated electrode support 216 of the ground trace 210. The bridge 220 tapers down in width as it travels to the sensor ground pad 218. In some embodiments, the bridge 220 has a relatively uniform and thin width to enable a desired amount of flexibility. The elongated electrode support 216 tapers down in width at its proximal end, however, this is not required. In some embodiments, the elongated electrode support 216 can abruptly transition to a much thinner trace at its proximal portion, to enable a desired amount of flexibility. Generally, the curvature of the traces where necking is shown is optimized to reduce balloon recapture forces and the potential for any snagging that sharper contours may present. The shape and position of the traces are also optimized to provide dimensional stability to the electrode assembly 200 as a whole, so as to prevent distortion during deployment and use. The ground trace 210 and active electrode trace 212 of FIG. 1D share a similar construction. The active electrode trace 212 also includes an elongated electrode support 216.

In FIG. 1D (prior art), an electrode 222 is layered over a portion of the insulating layer 202, which has a plurality of passages (e.g., holes) to enable the electrode 222 to couple to the elongated electrode support 216 of the ground trace 210 (of conductive layer 204).

As shown in FIG. 1D (prior art), the ground electrode trace 210 and active electrode trace 212 can include a plurality of electrodes. Three electrodes 222 are provided for each electrode trace, however, more or less can be used. Additionally, each electrode 222 can have radiused corners (e.g., rounded corners, etc.) to reduce tendency to snag on other devices and/or tissue. Although the above description of the electrodes 222 and the traces associated with them has been described in the context of a bi-polar electrode assembly, those of skill in the art will recognize that the same electrode assembly may function in a monopolar mode as well.

The sensor trace 214 may be centrally located on the distal electrode pad 208 and may include a sensor power pad 224 facing the sensor ground pad 218. These pads may connect to power and ground poles of a temperature sensor 226, such as a thermocouple (for example, Type T configuration: Copper/Constantan) or thermistor. The temperature sensor 226 may be proximately connected to the sensor power pad 224 and may be distally connected to the sensor ground pad 218.

From the distal electrode pad 208, the combined base layer 202, conductive layer 204, and insulating layer 206 may reduce in lateral width to an intermediate tail 228. Here, the conductive layer 204 may be formed to include an intermediate ground line 230, intermediate active electrode line 232, and intermediate sensor line 234, which may be respectively coextensive traces of the ground trace 210, active electrode trace 212, and sensor trace 214 of the distal electrode pad 208.

From the intermediate tail 228, the combined base layer 202, conductive layer 204, and insulating layer 206 may increase in lateral width to form a proximal electrode pad 236. The proximal electrode pad 236 may be constructed similarly to the distal electrode pad 208, with the electrode geometry and temperature sensor arrangement being essentially identical, although various differences may be present. However, as shown, the proximal electrode pad 236 may be laterally offset from the distal electrode pad 208 with respect to a central axis G-G extending along the intermediate ground line 230. The intermediate active electrode line 232 and intermediate sensor line 234 may be laterally coextensive with the proximal electrode pad 236 on parallel respective axes with respect to central axis G-G.

From the proximal electrode pad 236, the combined base layer 202, conductive layer 204, and insulating layer 206 may reduce in lateral width to form a proximal tail 238. The proximal tail 238 may include a proximal ground line 240, proximal active electrode line 242, and proximal sensor line 244, as well the intermediate active electrode line 232 and intermediate sensor line 234. The proximal tail 238 may include connectors (not shown) to enable coupling to one or more sub-wiring harnesses and/or connectors and ultimately to control unit 110. Each of these lines may be extended along parallel respective axes with respect to central axis G-G.

Figure 2A:
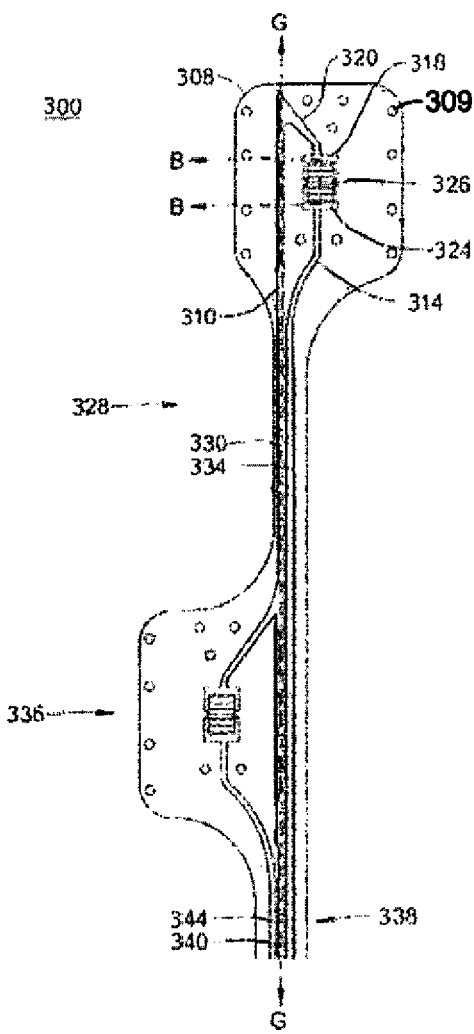
FIG. 2A is a top view of a flexible circuit including a thermistor assembly according to one or more embodiments of the present disclosure.
Figure 2B:
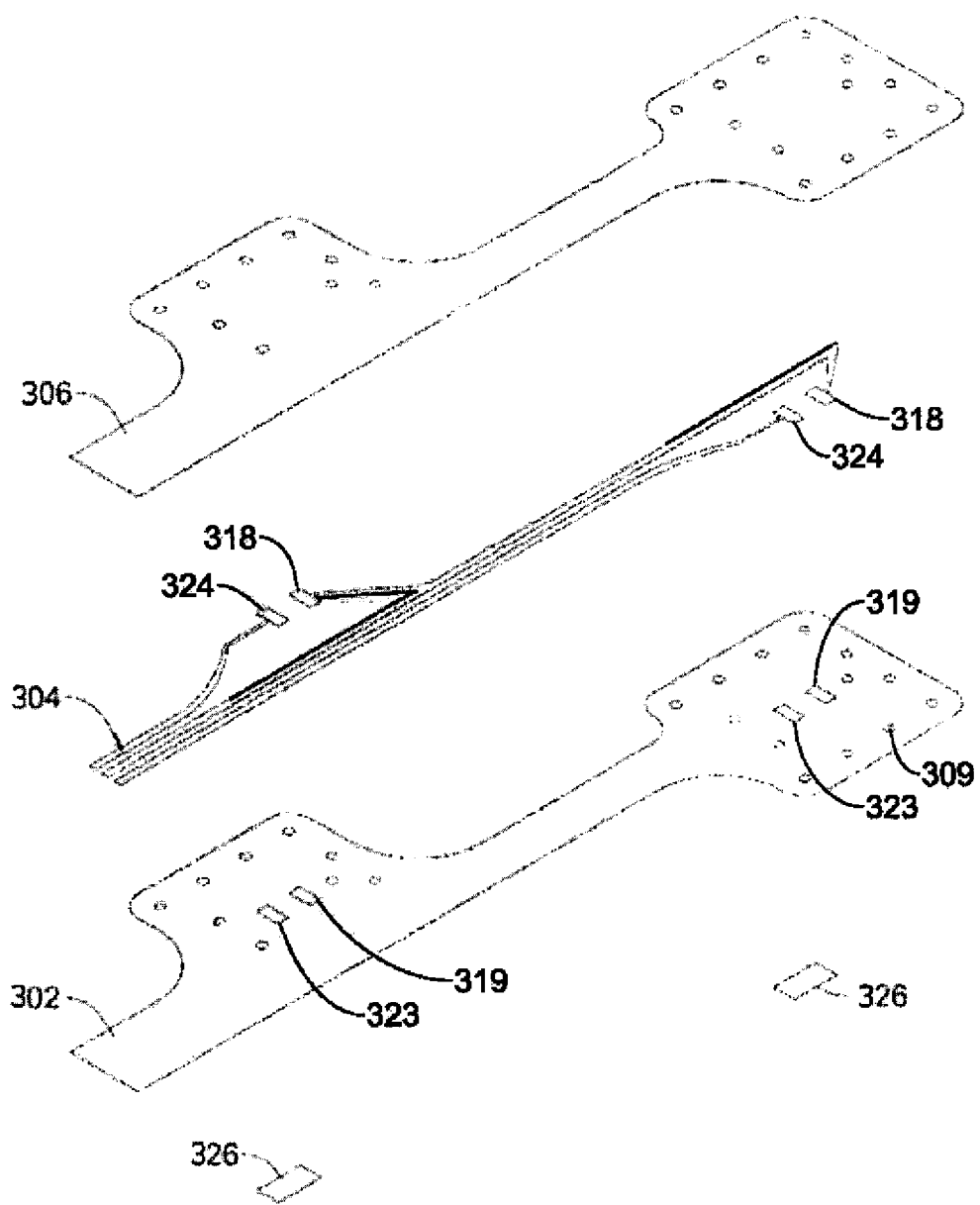
FIG. 2B is an exploded view of the thermistor assembly of FIG. 2A.
Figure 2C:
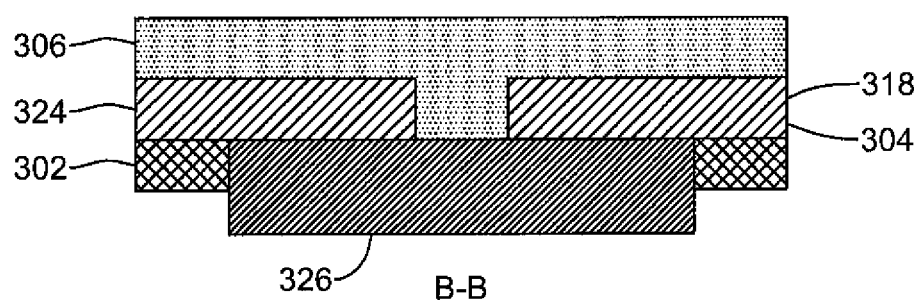
FIG. 2C is partial cross-sectional view B-B of FIG. 2A according to one or more embodiments of the present disclosure.
Figure 2D:
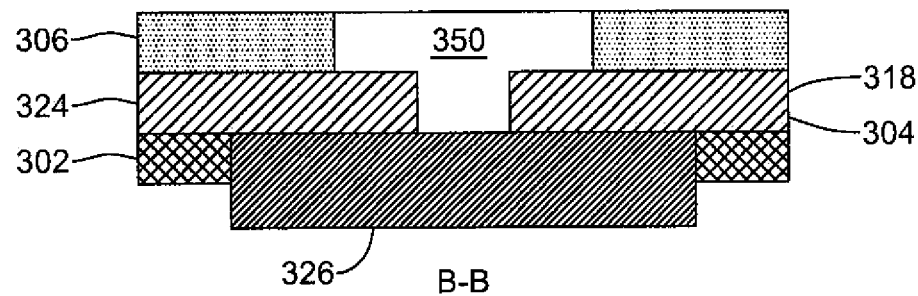
FIG. 2D is an alternative partial cross-sectional view B-B of FIG. 2A according to one or more embodiments of the present disclosure.

FIG. 2A shows a top view of thermistor assembly 300 according to one or more embodiments of the present disclosure. In one or more embodiments, the thermistor assembly 300 may be constructed as a flexible circuit having a plurality of layers, as shown in FIG. 2A. Such layers can be continuous or noncontiguous, i.e., made up of discrete portions. A base layer 302 (similar to base layer 202 described herein), as shown in FIGS. 2B-2D, of insulation provides a foundation for the thermistor assembly 300.

The base layer 302 can be constructed from a polymer film such as polyimide or a flexible polymer. In some embodiments, the base layer 302 is approximately 0.010 mm thick to about 0.020 mm thick (e.g., 0.5 mil (0.0127 mm) thick, etc.). As shown in FIGS. 2C and 2D, a conductive layer 304 made up of a plurality of discrete conductive traces is layered on top of the base layer 302. In some embodiments, the plurality of discrete conductive traces may be separated laterally by a non-conductive material, such as portions of the insulating layer 306. The conductive layer 304 can be, for example, a layer of electrodeposited copper or rolled-annealed copper. Other suitable conductive materials are also contemplated, such as graphene and other carbon-based materials. In some embodiments, the conductive layer 304 is approximately 0.010 mm to about 0.030 mm thick (e.g., 0.018 mm thick), among other suitable thicknesses. An insulating layer 306 may be discretely or continuously layered on top of the conductive layer 304, such that the conductive layer 304 is fluidly sealed between the base layer 302 and the insulating layer 306. In other words, the insulating layer 306 may form a top side or surface of the thermistor assembly 300 that may face away from the outer surface of the expandable member 30. The shape of insulating layer 306 and the shape of the insulating layer 302 may be the same (e.g., coextensive) or different. Like the base layer 302, the insulating layer can be constructed from a flexible polymer such as polyimide. In some embodiments, the insulating layer 306 is approximately 0.010 mm thick to about 0.020 mm thick (e.g., 0.5 mil (0.0127 mm) thick, etc.). In other embodiments, the insulating layer 306 is a complete or partial polymer coating, such as PTFE or silicone.

In one or more embodiments, the thermistor 326 is independently connected to the source of electric current 10. In such scenarios, a first sensor trace 314 may carry current from the source of electric current 10 to the thermistor 326 and the second wire 320 may carry current from the thermistor 326 to the source of the electric current 10 thereby completing the circuit. The first sensor trace 314 can be a cathode wire such that the first sensor trace 314 may be connected to a positive terminal of the source of electric current 10 and the second wire 320 can be an anode wire such that the second wire 320 may be connected to a negative terminal of the source of electric current 10. The first sensor trace 314 and the second wire 320 are electrically connected (e.g., attached) to the thermistor 326 directly or indirectly and extend proximally to the source of electric current 10. The first sensor trace 314 and the ground trace 310 may be connected to the thermistor 326 and the source of electric current 10 such that upon activation of the source of electric current 10, current may travel through the thermistor 326, thereby heating the thermistor 326. In one or more embodiments, the first sensor trace 314 and the ground trace 310 may extend within a lumen of the balloon catheter 20 and/or within the wall of balloon catheter 20 and the balloon wall and may be insulated.

In one or more embodiments, the thermistors 326 may be operatively engaged with the source of the electric current 10 through a first sensor trace and to an independent ground through a second wire. In one or more embodiments, each thermistor circuit includes two wires for operation.

In one or more embodiments, the plurality of thermistors 326 may be operatively coupled to the source of electric current 10 through the first sensor traces independently and are associated with the shared ground through the second traces (e.g., wires). In one or more embodiments, the plurality of thermistors 326 may be connected in series through a single first sensor trace.

The thermistor(s) 326 may be a hot end thermistor in which the thermistor 326 can both heat the target tissue to a desired temperature and provide feedback to a power and control unit, such as the source of electric current 10, regarding the current temperature of the thermistor and/or the temperature of the tissue adjacent to the thermistor 326. For example, as the temperature of the thermistor 326 increases or decreases, the resistance of the thermistor 326 will change. A power and control unit or other monitoring device, may determine the temperature of the thermistor 326 based on the measured resistance. It is contemplated that the power and/or frequency of the electrical current supplied to the thermistor 326 can be adjusted to achieve the desired temperature either manually by a clinician or automatically by the power and control unit. For example, the power and control unit may be programmed with a control algorithm configured to control the power, frequency, or other parameters of the electrical current to achieve a desired treatment temperature or temperature profile.

In some embodiments, the thermistor 326 may be made from a Curie temperature material. In addition to heating the target tissue and providing feedback regarding the current temperature, a Curie temperature thermistor may also provide an upper limit on how hot the thermistor 326 can get. For example, the thermistor 326 may heat only in the presence of a specified electric or magnetic field and frequency and only to the Curie temperature of the thermistor 326. When the Curie temperature is reached, the material goes from magnetic to non-magnetic, discontinuing the heating. This is a cyclic process that permanently and rapidly maintains the thermistor 326 temperature at the set Curie point of the material, as long as the electric or magnetic field is applied. In some instances, an electromagnetic coil or magnetic generator may be provided within or on the device to generate a magnetic field in close proximity to the Curie temperature material, as will be discussed in more detail below with respect FIG. 3.

FIG. 2B is an exploded view of the thermistor assembly 300 shown in FIG. 2A, further illustrating the layers of the thermistor assembly 300. For example, as shown in FIG. 2B, the conductive layer 304 is disposed between the first insulating layer, or base layer 302 and the second insulating layer 306. In one or more embodiments, each of the sensor ground pad 318 and sensor power pad 324 is aligned with an aperture 319, 323 through the base insulating layer 302 whereby it can make contact with a thermistor 326.

The thermistor assembly 300 shown in FIG. 2A includes a distal thermistor pad 308. In this region, the base layer 302 forms a generally rectangular shape. As shown, the thermistor assembly 300 may include a plurality of openings to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure.

The distal thermistor pad 308 includes a plurality of discrete traces layered on top of the base layer 302. These traces include a ground trace 310 and a sensor trace 314. The ground trace 310 extends laterally offset from a sensor ground pad 318. The sensor ground pad 318 is electrically coupled to the ground trace 310 and is shown in FIG. 2A to be centrally located on the distal thermistor pad 308. In one or more embodiments, the sensor ground pad 318 is not centrally located on the distal thermistor pad 308. In some embodiments, the ground trace 310 has a relatively uniform and thin width to enable a desired amount of flexibility. In some embodiments, the sensor ground pad 318 can abruptly transition to a much thinner trace, to enable a desired amount of flexibility. Generally, the curvature of the traces where necking is shown may be selected to reduce balloon recapture forces and the potential for any snagging that sharper contours may present. The shape and position of the traces may be selected to provide dimensional stability to the thermistor assembly 300 as a whole, so as to prevent distortion during deployment and use.

The sensor trace 314 is centrally located on the distal thermistor pad 308 and includes a sensor power pad 324 facing the sensor ground pad 318. These pads can connect to power and ground poles of a heat sensing device 326, such as a thermistor, as shown in the partial cross-section depicted in FIG. 2C.

In FIG. 2A, thermistor 326 (e.g., heat sensing device) is proximally connected to the sensor power pad 324 and distally connected to the sensor ground pad 318. To help reduce overall thickness of the flexible circuit, thermistor 326 may be positioned within an opening 303 within the base layer 302, as shown in FIGS. 2C-2D. In some embodiments, thermistor 326 has a thickness of 0.1 mm, which is approximately two-thirds of industry standard. As shown, thermistor 326 is on a non-tissue contacting side of the distal thermistor pad 308. Accordingly, thermistor 326 is captured between the insulating layer 306 and a balloon, or other portion a medical device, when incorporated into a final device. Surface-mounted electrical components, like thermistors, have been known to have sharp edges and corners, which can get caught on tissue and possibly cause problems (e.g., related to balloon robustness) during balloon deployment and/or retraction. The arrangement of FIGS. 2C and 2D also keeps soldered connections from making contact with blood, since solder is typically non-biocompatible.

In one or more embodiment, the heat generated by the thermistor 326 may be more efficiently transferred to the medical device's surroundings by including a material 350 having increased thermal conductivity, relative to the second insulating layer 306, positioned at least partially within the second insulating layer 306, as shown in FIG. 2D. As also shown in FIG. 2D, material 350 is in contact with the at least one thermistor 326.

From the rectangular distal thermistor pad 308, the combined base layer 302, conductive layer 304, and insulating layer 306 reduce in lateral width to an intermediate tail 328. Here, the conductive layer 304 is formed to include an intermediate ground line 330 and an intermediate sensor line 334, which are respectively coextensive traces of the ground trace 310 and sensor trace 314 of the distal thermistor pad 308.

From the intermediate tail 328, the combined base layer 302, conductive layer 304, and insulating layer 306 increase in lateral width to form a proximal thermistor pad 336. The proximal thermistor pad 336 is constructed similarly to the distal thermistor pad 308, with the thermistor arrangement being essentially identical, although various differences may be present in one or more embodiments. However, as shown in FIG. 2A, the proximal thermistor pad 336 is laterally offset from the distal thermistor pad 308 with respect to a central axis G-G extending along the intermediate ground line 330. The intermediate sensor line 334 is laterally coextensive with the proximal thermistor pad 336 on parallel respective axes with respect to central axis G-G.

From the proximal thermistor pad 336, the combined base layer 302, conductive layer 304, and insulating layer 306 reduce in lateral width to form a proximal tail 338. The proximal tail 338 includes a proximal ground line 340 and proximal sensor line 344, as well as the intermediate sensor line 334. The proximal tail 338 includes connectors (not shown) to enable coupling to one or more sub-wiring harnesses and/or connectors and ultimately to control unit 10. Each of these lines extends along parallel respective axes with respect to central axis G-G.

Figure 2E:
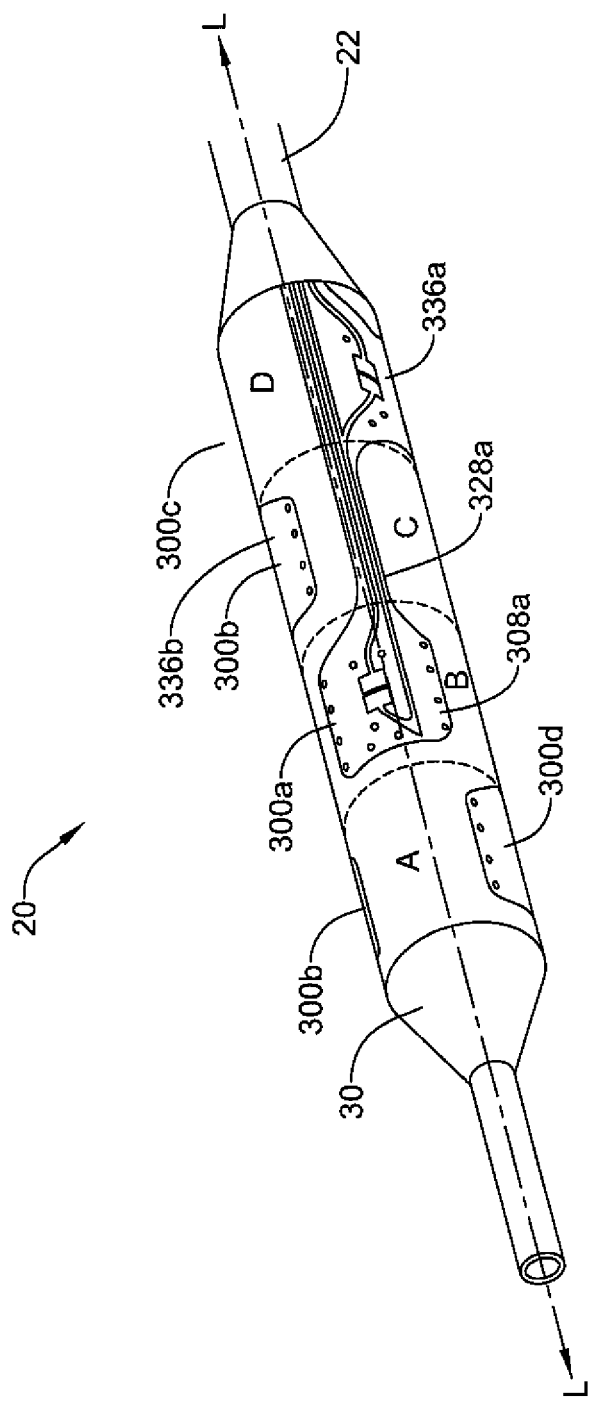
FIG. 2E is a perspective view of an expandable device of a catheter.

The thermistor assembly 300 shown in FIGS. 2A and 2B includes a thermistor array that includes two thermistors 326, a first thermistor that is located on the proximal thermistor pad 336 and a second thermistor that is located on the distal thermistor pad 308. For example, as seen in FIG. 2E, a helical line may be drawn connecting the two thermistors of thermistor assembly 300a. It may be noted that the embodiment of FIG. 2E includes additional thermistor arrays. For example, each of thermistor assemblies 300b, 300c (not shown; located on balloon 30 opposite thermistor assembly 300a), and 300d include a thermistor array that includes two thermistors. Furthermore, each of the treatment zones A-D includes a thermistor array that includes the two thermistors located in that treatment zone, such as the thermistor of the distal thermistor pad of thermistor assembly 300a and the thermistor of the distal thermistor pad of thermistor assembly 300c (not shown), which is located on the opposite side of the expandable balloon (e.g., oriented circumferentially 180 degrees from thermistor assembly 300a).

As shown, the thermistor assembly 300 has an asymmetric arrangement of the distal thermistor pad 308 and proximal thermistor pad 336, about axis G-G. It has been found that this arrangement is useful. For example, by essentially sharing the same ground trace, the width of the proximal tail is narrower than only about one and a half times that of the intermediate tail 328, rather than being approximately twice as wide if each thermistor pad had independent ground lines. Thus, the proximal tail 338 is narrower than two of the intermediate tails 328.

Figure 2F:
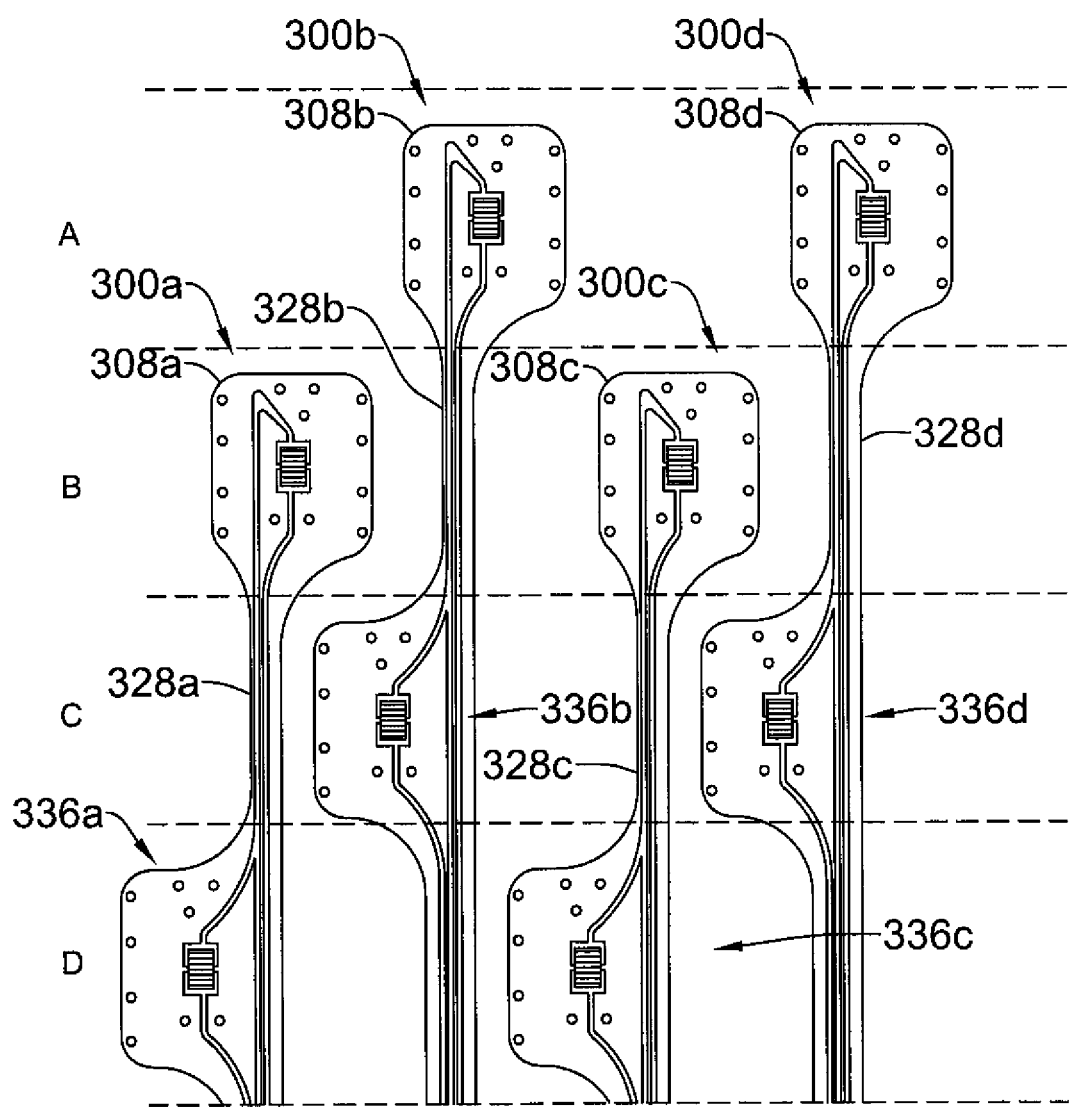
FIG. 2F is a top view of the expandable device of FIG. 2E in an unrolled configuration

Referring to FIGS. 2A, 2E, and 2F, the thermistor pad arrangement of each thermistor assembly 300a-d also enables efficient placement of the assemblies 300a-d on a balloon 30. As shown in FIGS. 2E and 2F, the thermistor assemblies 300a-d "key" into one another to enable maximum use of balloon surface area. This is accomplished in part by spacing the thermistor pads apart by setting the longitudinal length of each intermediate tail. For example, the intermediate tail length 328a of thermistor assembly 300a is set to a distance that separates its distal and proximal thermistor pads 308a, 336a such that the laterally adjacent proximal thermistor pad 336b of the laterally adjacent thermistor assembly 300b keys next to the intermediate tail 328a of thermistor assembly 300a. Further, the distal thermistor pad 308a of thermistor assembly 300a is keyed between the intermediate tail 328b of thermistor assembly 300b and the intermediate tail 328d of thermistor assembly 300d. Thus, the length of each intermediate tail 328a-d also requires each thermistor pad of any one thermistor assembly to be located in non-adjacent treatment zones.

Increasing balloon surface area utilization is also enabled in part by laterally offsetting both thermistor pads of each thermistor assembly 300a-d. For example, the rightwards lateral offset of each distal thermistor pad 308a-d and the leftwards lateral offset of the proximal thermistor pad 336a-d allow adjacent thermistor pad assemblies to key into one another such that some of the thermistor pads laterally overlap one another. For example, the distal thermistor pad 308a of thermistor assembly 300a laterally overlaps with proximal thermistor pad 336b of thermistor assembly 300b, as shown in FIG. 2F. Further, the distal thermistor pad 308b of thermistor assembly 300b laterally overlaps with the proximal thermistor pad 336c of thermistor assembly 300c. However, the length of each intermediate tail prevents circumferential and/or longitudinal overlap of the thermistor pads, thus maintaining the non-contiguous nature of the treatment zones in the longitudinal direction L-L, as shown in FIG. 2E.

The arrangement and geometry of the thermistor pads, as well as the arrangement and geometry of the tails of the flexible circuits may also facilitate folding, or refolding, or otherwise collapsing the balloon into a relatively compact, low-profile, un-expanded state. For instance, in embodiments with an expanded diameter of up to 10 mm, the device in an un-expanded state may have a diameter as low as approximately 1 mm.

Some embodiments utilize a standard thermistor assembly, such as, but not limited to assembly 300, having identical dimensions and construction, wherein the number and relative position of thermistor assemblies on an outer surface of a balloon becomes a function of balloon diameter and/or length while thermistor assembly geometries remain unchanged amongst various balloon sizes. The relative positioning of thermistor assemblies relative to balloon diameter and/or length may then be determined by the desired degree, or avoidance of circumferential and/or axial overlap, of adjacent thermistor pads of neighboring thermistor assemblies on a balloon of a given size. In other embodiments, however, all of the thermistor assemblies on the balloon will not necessarily be identical.

It should be noted that the generally rectangular shape of the proximal thermistor pads 336a-d and the distal thermistor pads 308a-d may have any suitable size (e.g., any suitable length, any suitable width, etc.) and any suitable shape (e.g., any geometric shape, any irregular shape, etc.). For example, a thermistor assembly 300 having a proximal thermistor pad 336 and/or a distal thermistor pad 308, each having a reduced lateral dimension (e.g., having a reduced margin or distance between the edge of the proximal thermistor pad 336 and/or distal thermistor pad 308 relative to the edges of respective conductive traces and thermistors thereon, etc.), would allow an increased number of thermistor assemblies to be arranged circumferentially around a given balloon circumference. In one or more embodiments, a thermistor assembly may include an increased number of thermistors arranged generally longitudinally. For example, in one or more embodiments, a thermistor assembly may include, in addition to the aforementioned proximal thermistor pad (e.g., a first thermistor pad having a first thermistor) and the distal thermistor pad (e.g., a second thermistor pad having a second thermistor), additional thermistor pads wherein each thermistor pad may include one or more thermistors. In one or more embodiments, a thermistor assembly 300 may include a third thermistor arranged, for example, with the same lateral offset from the distal thermistor as the proximal thermistor (e.g., in the same or opposite direction) and/or with the same longitudinal offset from the distal thermistor in the opposite direction. In one or more embodiments, a thermistor assembly 300 may include a fourth thermistor arranged, for example, with the same lateral offset from the third thermistor as the distal thermistor (e.g., in the same or opposite direction) and/or with the same longitudinal offset from the third thermistor in the opposite direction. Likewise, a thermistor assembly 300 may include any suitable number of thermistors on any suitable number of thermistor pads.

In one or more embodiments, a thermistor assembly 300 may include one or more holes in the first and/or second insulting layers to increase flexibility of the thermistor assembly, which may make balloon expansion and balloon collapsing easier or may improve mechanical anchorage of an adhesive used to affix the thermistor assembly 300 to the expandable device or device.

Returning to FIG. 2E, the treatment zones A-D are longitudinally adjacent to one another along longitudinal axis L-L, and may be configured such that energy applied by the thermistor assemblies create treatments that do not overlap. Treatments applied by the longitudinally adjacent thermistor assemblies are circumferentially non-continuous along longitudinal axis L-L. For example, with reference to FIG. 2E, lesions created in treatment zone A may, in some embodiments, minimize overlap about a circumference (circumferentially with respect to L-L in this view) with lesions created in treatment zone B.

In one or more embodiments, however, the energy applied by the thermistor assemblies, such as the thermistor assemblies 300a-d shown in FIG. 2E, may overlap, longitudinally, circumferentially, and/or in other ways, to at least some extent.

Each adjacent thermistor 326 may be associated with a treatment zone (or may be configured to create such a treatment zone in a tissue in apposition with the thermistors) that includes a target temperature zone (having an outer boundary) and a thermal plume (having an outer boundary extending around the outer boundary of the target temperature zone). In some embodiments, the target temperature zone represents a region of the tissue that is at or above a desired target treatment temperature, or is within a desired target temperature range. In some embodiments, the thermal plume represents a region of the tissue that is not necessarily at a target temperature or within a target temperature range, but exhibits an increase in temperature relative to an untreated zone outside of the thermal plume.

The existence of and extent of overlap of the treatment zones from adjacent thermistors 326 may be influenced by a wide variety of factors, including, but not limited to, thermistor geometry, thermistor placement density, thermistor positioning, energy generator output settings, output voltage, output power, duty cycle, output frequency, tissue characteristics, tissue type, etc.

In some embodiments, an individual thermistor 326 may each define its own treatment zone, and such treatment zones may partially, or entirely, overlap with a treatment zone of another individual thermistor.

In one or more embodiments, the thermal plumes of the treatment zones overlap, although the target temperature zones might not. In one or more embodiments, both the target temperature zones and their thermal plumes overlap. In some embodiments, the overlap of treatment zones may extend substantially continuously around a circumference of the device and/or around a circumference in a tissue surrounding a body passageway. In other embodiments, there may be overlap in treatment zones, however, that overlap will not be substantially continuous around a circumference and significant discontinuities in the treatment zones may be present.

In one or more embodiments, an array of balloon-mounted thermistors, such as thermistors 326, can create overlapping treatment zones between adjacent thermistors, and, in at least some instances, create treatment zones that are effectively substantially continuous about a circumference of a body passageway. For example, an expandable balloon, such as balloon 30, may include several longitudinally extending series of thermistors positioned about the circumference of the balloon. In one or more embodiments, thermistors (e.g., thermistor arrays) are arranged symmetrically on the expandable balloon.

However, the shown configuration of thermistors 326 is not a necessary requirement, since thermistor size and placement geometry can vary according to desired therapeutic effect.

In another aspect of the present disclosure, a method of nerve modulation includes receiving a medical device that includes a balloon catheter, such as catheter device 20. The balloon catheter 20 includes a balloon, such as balloon 30 that has a balloon wall and is structured and arranged to be disposed within a vessel that defines a vessel lumen. The balloon catheter also includes at least one thermistor array, such as thermistor assembly 300, disposed on the balloon wall, the at least one thermistor array including at least two thermistors, such as thermistors 326. As otherwise discussed herein, the thermistor array is operatively engaged with a source of electric current and each of the at least two thermistors has a resistance that varies with temperature. The method of nerve modulation also includes disposing the at least one thermistor array proximate (e.g., near) a nerve to be modulated and transferring heat from the medical device to the nerve to modulate the nerve, wherein at least 50 percent of the heat transferred from the medical device is generated by resistance heating. In one or more embodiments, transferring heat from the medical device includes heating the at least two thermistors. In some embodiments, heating the at least two thermistors may include providing an electric current to the at least two thermistors, resulting in resistive heating of the at least two thermistors. In one or more embodiments, transferring heat from the medical device includes also monitoring the temperature of the at least two thermistors by measuring electrical resistance. In some embodiments, electrical resistance may be measured by a control system, such as control system 10 described herein. In some embodiments, the measured electrical resistance may be correlated to a temperature of the thermistor.

An operator may manipulate the source of electric current 10 to deliver a selected amount of electric current to the thermistors 326. Alternatively, the source of electric current may be automatically controlled by a control algorithm within control unit (either integrated with the source 10 or a separate unit in addition to the source 10). In one or more embodiments, the resistance of at least one thermistor 326 may vary with temperature. When the thermistor 326 is subjected to an electric current, the temperature of thermistor 326 may increase as a result of the electrical resistance. In one or more embodiments, the heat generated at the thermistor 326 may be transferred to the environment near thermistor 326 (e.g., tissue at the treatment location in contact with the thermistor 326, thereby modulating one or more nerves in that region, etc.).

In one or more embodiments, the temperature of at least one the thermistor 326 and the treatment location may be measured (e.g., in real time) while simultaneously providing heat to the treatment location. The operator may operate the medical device 40 at a constant voltage and measure the electric current across the at least one thermistor 326. The measured electric current can be used to determine (e.g., calculate, etc.) real-time resistance of the at least one thermistor 326. Since the variation of the resistance of the at least one thermistor 326 with respect to temperature is known and/or can be calibrated, the temperature of the at least one thermistor 326 can be determined. In such embodiments, no additional temperature measuring sensors and circuitry is required. In one or more embodiments, the elimination of additional temperature measuring sensors and circuitry may reduce the complexity of the circuit and may reduce the cost of manufacturing, operating and/or maintaining the device, and improve the overall profile of the device accordingly. In one or more embodiments, the elimination of the need for an additional temperature measuring sensor and/or additional circuitry reduces the circuit to have a minimum of two wires instead of three, four, five, and so on.

In one or more embodiments, more than one thermistor 326 is connected to the negative terminal of the source of electric current 10 through a shared ground trace 310. This may reduce the number of second ground traces 310 in the circuit, thereby reducing the total number of wires and hence, complexity of the circuit. However, because the thermistors 326 are connected individually to each discrete positive terminal of the source of electric current control 10 through the first sensor traces 314, the current through each of the thermistors 326 may be independently controlled. In one or more embodiments, more than one thermistor 326 may be connected in parallel (e.g., to measure each the current and resistance of each thermistor and be able to convert to temperature).

In one or more embodiments, the thermistor 326 may be a switching positive temperature coefficient ("PTC") thermistor, wherein one could override the temperature control unit. With a PTC thermistor, the resistance increases dramatically as the temperature increases above the so-called Curie temperature. In one or more embodiments, the PTC thermistor includes a material having a Curie temperature of less than 100 degrees Celsius (e.g., about 60 Celsius). In one or more embodiments, switching-type PTC thermistors may be formed from or include one or more polycrystalline materials (e.g., fabricated using mixtures of barium carbonate, titanium oxide and additives like tantalum, silica, and manganese). In some embodiments, the materials are ground, mixed, compressed into disks or rectangle shapes, and sintered. In some embodiments, a thermistor may include a polymer PTCs made of a slice of plastic with carbon grains embedded in it. When such a device is cool, the carbon grains are in close contact with each other, forming a conductive path through the device. As the device heats up, the plastic expands and the grains move further apart, raising the total resistance of the device. Further information regarding types of thermistors may be found at "PTC Thermistor," University of Technology Eindhoven, 2014, available at http://www.resistorguide.com/ptc-thermistor/(last accessed on Mar. 25, 2014) the full disclosure of which is incorporated herein by reference. In one or more embodiments in which a thermistor is a PTC-type thermistor, the thermistor may include a self-limiting (current) safety feature regarding temperature. For example, as the temperature increases, the resistance could increase as well, limiting the current passing through the device and lowering the temperature.

As the number of electrical components and the traces (e.g., wires) are reduced, the overall profile of the balloon catheter 20 may also get reduced, for example, in the collapsed (e.g., wrapped, folded, etc.) state. Manufacturing procedures may also be simplified and cost of manufacturing the device 40 may also be reduced.

Figure 3:
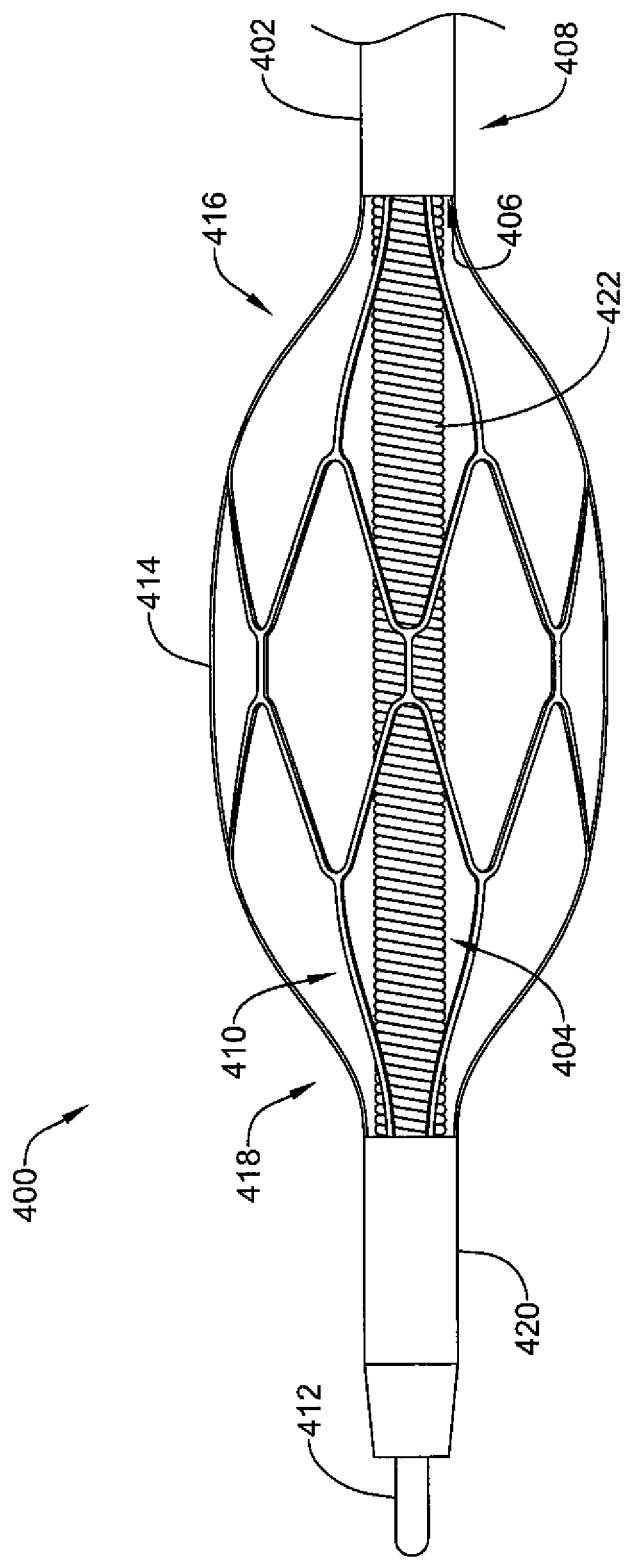
FIG. 3 is a side view of a distal portion of another illustrative expandable device.
Figure 4:
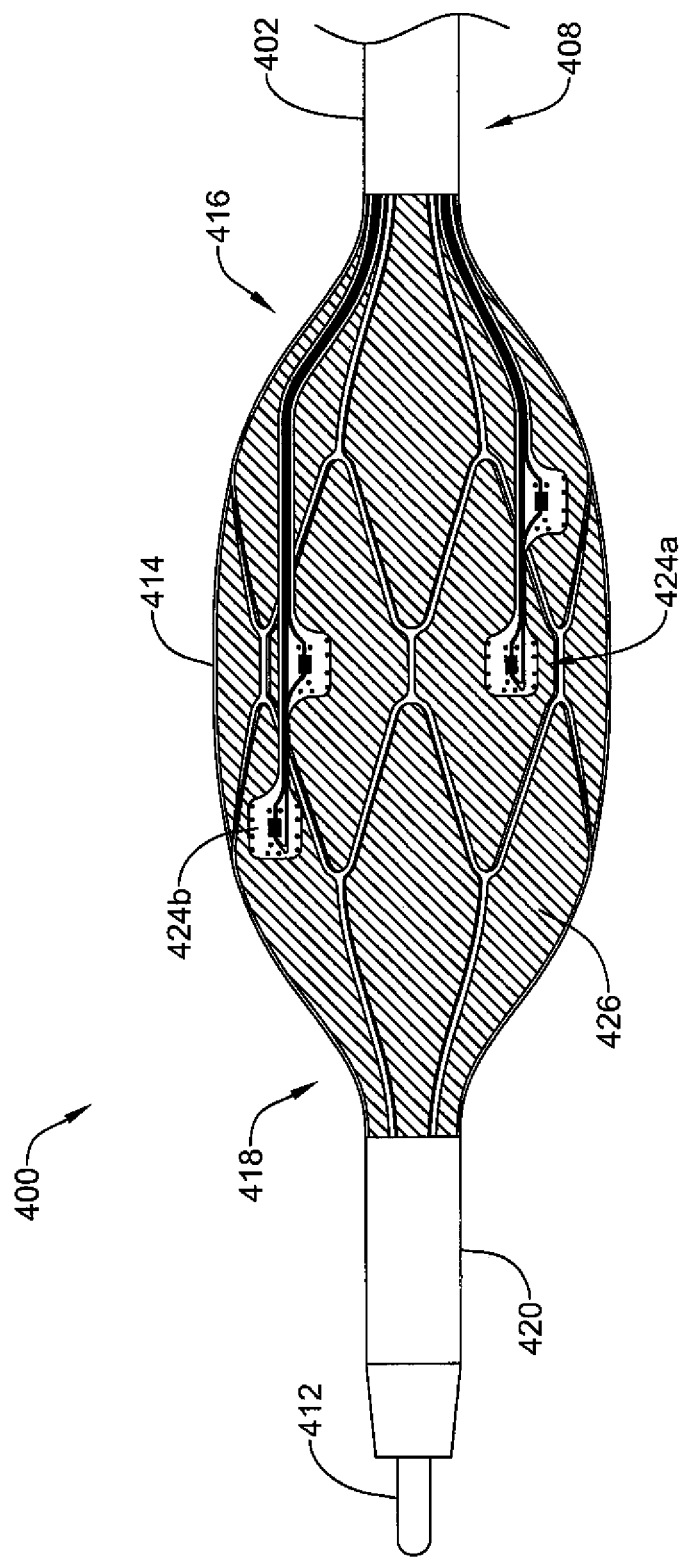
FIG. 4 is another side view of the illustrative expandable device of FIG. 3.

FIGS. 3 and 4 illustrate a distal portion of another illustrative nerve or tissue modulation or ablation device 400 having a basket structure covered with a coating. Referring first to FIG. 3, the modulation system 400 may include a catheter shaft having an outer elongate shaft 402 and an inner elongate shaft 404. The outer elongate shaft 402 may extend proximally from a distal end region 408 to the proximal end configured to remain outside of a patient's body. The inner elongate shaft 404 may be slidably disposed within a lumen 406 of the outer elongate shaft 402. The inner elongate shaft 404 may extend proximally from a distal end region 410 to a proximal end configured to remain outside of a patient's body. Although not shown, the proximal ends of the inner and/or outer elongate shafts 404, 402 may include a hub attached thereto for connecting other treatment devices or providing a port for facilitating other treatments. It is contemplated that the stiffness of the inner and/or outer elongate shafts 404, 402 may be modified to form a modulation device 400 for use in various vessel diameters and various locations within the vascular tree.

In some instances, the inner and/or outer elongate shafts 404, 402 may have an elongate tubular structure and may include one or more lumens extending therethrough. For instance, in the illustrated embodiment, the outer elongate shaft 402 may include a lumen 406 for slidably receiving the inner tubular shaft 404. The inner tubular shaft 404 may include a lumen (not explicitly shown) having a guidewire wire 412 slidably disposed therein. In some instances, the modulation device 400 may have a fixed wire distal end with no guidewire lumen. These are just examples. In some embodiments, the inner and/or outer elongate shafts 404, 402 may include one or more auxiliary lumens. In some instances, the inner and/or outer elongate shafts 404, 402 may include a separate lumen(s) (not shown) for infusion of fluids, such as saline or dye for visualization or for other purposes such as the introduction of a medical device, and so forth. The fluid may facilitate cooling of the modulation device 400 during the ablation procedure, in addition to the cooling of a body lumen. Further, the lumens may be configured in any way known in the art. For example, the lumen(s) may extend along the entire length of the inner and/or outer elongate shafts 404, 402 such as in an over-the-wire catheter or may extend only along a distal portion of the inner and/or outer elongate shafts 404, 402 such as in a single operator exchange (SOE) catheter. These examples are not intended to be limiting, but rather examples of some possible configurations. While not explicitly shown, the modulation device 400 may further include temperature sensors/wire, an infusion lumen, radiopaque marker bands, fixed guidewire tip, a guidewire lumen, and/or other components to facilitate the use and advancement of the device 400 within the vasculature.

Further, the inner and/or outer elongate shafts 404, 402 may have a relatively long, thin, flexible tubular configuration. In some instances, the inner and/or outer elongate shafts 404, 402 may have a generally circular cross-section, however, other suitable configurations such as, but not limited to, rectangular, oval, irregular, or the like may also be contemplated. In addition, the inner and/or outer elongate shafts 404, 402 may have a cross-sectional configuration adapted to be received in a desired vessel, such as a renal artery. For instance, the inner and/or outer elongate shafts 404, 402 may be sized and configured to accommodate passage through an intravascular path, which leads from a percutaneous access site in, for example, the femoral, brachial, or radial artery, to a targeted treatment site, for example, within a renal artery.

In some embodiments, the device 400 may further include an electromagnetic coil 422 disposed around the inner elongate shaft 404 and within an interior portion of the basket 414. Additional electromagnetic coils 422 may also be utilized either within the device 400 or at a location configured to be external to a patient's body. The electromagnetic coil 422 may be in electrical communication with a power and control unit configured to remain outside the body. The power and control unit may supply an electrical current to the coil 422 to generate a magnetic field. It is contemplated that the electrical current supplied to the coil 422 and/or the size of the coil 422 may be varied to generate the desired magnetic field.

The modulation device 400 may further include an expandable basket 414 having a proximal end 416 and a distal end 418. In the expanded form, the basket 414 may have a tapered proximal end 416 and a tapered distal end 418 and an enlarged central region, although this is not required. In some embodiments, the expandable basket 414 may be laser cut from a generally tubular member to form the desired pattern. While the expandable basket 414 is illustrated as having an open cell, generally stent-like, structure it is contemplated that the basket 414 may be formed to have any of a number of different configurations. For example, in some instances, the basket 414 may be formed from a number of generally longitudinally extending tines or may be formed from one or more filaments that may be woven, braided, knotted, etc. These are just examples. It is contemplated that the use of an expandable basket 414 may eliminate the need for an inflation lumen, thus reducing the overall profile of the modulation system 400. Other illustrative basket assemblies useable with the embodiments disclosed herein are disclosed in U.S. patent application Ser. No. 14/327,154 entitled "Devices And Methods For Nerve Modulation", the full disclosure of which is incorporated by reference herein.

It is contemplated that the expandable basket 414 can be made from a number of different materials such as, but not limited to, metals, metal alloys, shape memory alloys and/or polymers, as desired, enabling the basket 414 to be expanded into shape when positioned within the body. For example, the expandable basket 414 can be formed from alloys such as, but not limited to, nitinol or Elgiloy®. Depending on the material selected for construction, the basket 414 may be self-expanding or may require an actuation mechanism as will be discussed in more detail below. In some embodiments, fibers may be used to make the expandable basket 414, which may be cored fibers, for example, having an outer shell made of nitinol having a platinum core. It is further contemplated the expandable basket 414 may be formed from polymers including, but not limited to, polyether ether ketone (PEEK), nylon, polyethylene terephthalate (PET), polyimides, polyether block amides, etc.

The proximal end 416 of the basket 414 may be secured to or adjacent to the distal end region 408 of the outer elongate shaft 402. The distal end 418 of the basket 414 may be secured to or adjacent to the distal end region 410 of the inner elongate shaft 404. In some instances, the distal end 418 of the basket 414 may be secured directly to the inner elongate shaft 404. In other instances, the distal end 418 of the basket 414 may be secured to a mounting element 420. The mounting element 420 may be slidably disposed over the inner elongate shaft 404 or may be fixedly secured to the inner elongate shaft 404. As noted above, in some instances, the basket 414 may be self-expanding. It is contemplated that a self-expanding basket 414 may be maintained in a compressed (or collapsed state) when an external force is placed on the basket 414. The basket 414 may then expand when the external force is released. In such an instance, the basket 414 may be formed in the expanded state (as shown in FIG. 3) and compressed to fit within a delivery sheath. Upon reaching the target location, the delivery sheath can be retracted to deploy the expandable basket 414. It is contemplated that in some instances, the basket may be self-expanding without a capture sheath since the guide sheath could introduce it into the vessel and if the cover material made the basket 414 atraumatic enough so that it could be introduced into the artery while expanded.

In other embodiments, the system 400 may include an actuation mechanism, for example, a pull wire (not explicitly shown), which may be employed to manipulate or actuate the expandable basket 414 between the collapsed and expanded configurations. In an embodiment, the pull wire may be attached to the proximal end 416 or distal end 418 of the basket 414 such that a push-pull actuation of the pull wire may manipulate the expandable basket 414, thus actuating the expandable basket 414 between the collapsed and expanded configurations. In some instances, the pull wire may be pulled proximally to pull the expandable basket 414, moving the expandable basket 414 to the expanded configuration. In addition, the pull wire may be pushed distally to move the expandable basket 414 into the collapsed configuration. Alternatively, the pull wire may be pushed distally, which may allow the expandable basket 414 to move to the expanded state. In such an instance, the pull wire may be pulled proximally, which may allow the expandable basket 414 to move to the collapsed state.

FIG. 4 illustrates the modulation system 400 of FIG. 3 including additional components. The modulation system 400 may further include an inner cover or coating 426 disposed on an inner surface of the expandable basket 414. In some instances, the inner cover 426 may be adhered to the basket 414 using methods commonly known in the art. The inner cover 426 may be made from an elastomeric material, such as, but not limited to: polyurethane, silicone, etc. An elastomeric material may help close the basket 414 to its un-expanded configuration after use. However, in some instances, elastomers such as polyurethane may fail due the heat from ablation. To prevent this, the elastomer could be insulated around the thermistors with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 426 may extend from the proximal end 416 to the distal end 418 of the basket 414. However, this is not required. It is contemplated that the inner cover 426 may extend over any length or partial length of the basket 414 desired, or may not even be present.

The modulation system 400 may further include one or more thermistor assemblies 424a, 424b positioned on a surface of the expandable basket 414 and/or inner cover 426 for delivering heat to a desired treatment region. The thermistor assemblies 424a, 424b may be similar in form and function to the thermistor assemblies 300 described above. It is contemplated that the modulation system 400 may include any number of thermistor assemblies 424a, 424b desired based on the size of the modulation device 400 and/or the desired treatment region. For example, the modulation system may include one, two, three, four, five, or more thermistor assemblies. It is further contemplated that the thermistor assemblies 424a, 424b may be staggered about the circumference and/or length of the expandable basket 414 such that a maximum number of thermistor assemblies 424a, 424b can be positioned on the modulation device.

In some instances, one or more thermistor assemblies 424a, 424b may be positioned on or underneath a surface of an outer cover (not explicitly shown) positioned on an outer surface of the basket 414. It is contemplated that the outer cover may extend from the proximal end 416 to the distal end 418 of the basket 414. However, this is not required. It is contemplated that the outer cover may extend over any length or partial length of the basket 414 desired, or may not even be present. The inner 426 and outer covers may be formed of the same material or may be formed from different materials, as desired. In some embodiments, one or both of the inner 426 and/or outer covers may be omitted.

In some instances, the outer cover may be adhered to the inner cover 426 and/or basket 414 using methods commonly known in the art. Together, the inner 426 and outer covers may encase all or part of the thermistor assemblies 424a, 424b and the associated electronics. It is contemplated that the inner 426 and outer covers may fix the thermistor assemblies 424a, 424b more securely to the expandable basket 414 relative to securing assemblies to a traditional inflatable balloon as the inner 426 and outer covers sandwich the thermistor assemblies 424a, 424b and may be more amenable to covalent adhesive bonding. It is contemplated that affixing the thermistor assemblies 424a, 424b between at least the basket 414 and the outer cover may improve thermistor fixation to system since such an arrangement may eliminate or reduce thermistor catch points is not dependent on adhesive to fix the thermistor assemblies 424a, 424b to the modulation system. This may improve the safety of system 400.

When an outer cover is disposed over the thermistors, the thermistors may be in insulated contact with the desired treatment region. In some instances, the outer cover may not extend over the thermistors of the thermistor assemblies 424a, 424b. For example, the thermistors may be coated or covered with a masking material prior to application of the outer cover. Once the outer cover has been formed, the masking material may be removed to expose the thermistors. In some instances, the outer cover may be disposed over the thermistors and subsequently removed with techniques, such as, but not limited, to laser ablation. This may allow for the thermistors to directly contact the vessel wall. It is further contemplated that the outer cover may be removed from some of the thermistors independently (for example using parylene) to allow for some insulated contact with the desired treatment region.

In some embodiments, the thermistor on the thermistor assembly 424a, 424b may be made from a Curie temperature material. In addition to heating the target tissue and providing feedback regarding the current temperature, a Curie temperature thermistor may also provide an upper limit on how hot the thermistor can get. For example, the thermistor may heat only in the presence of a specified electric or magnetic field and frequency and only to the Curie temperature of the thermistor. When the Curie temperature is reached, the material goes from magnetic to non-magnetic, discontinuing the heating. This is a cyclic process that permanently and rapidly maintains the thermistor temperature at the set Curie point of the material, as long as the electric or magnetic field is applied. In some instances, an electromagnetic coil or magnetic generator, such as coil 422, may be provided within or on the device to generate a magnetic field in close proximity to the Curie temperature material.

Figure 5:
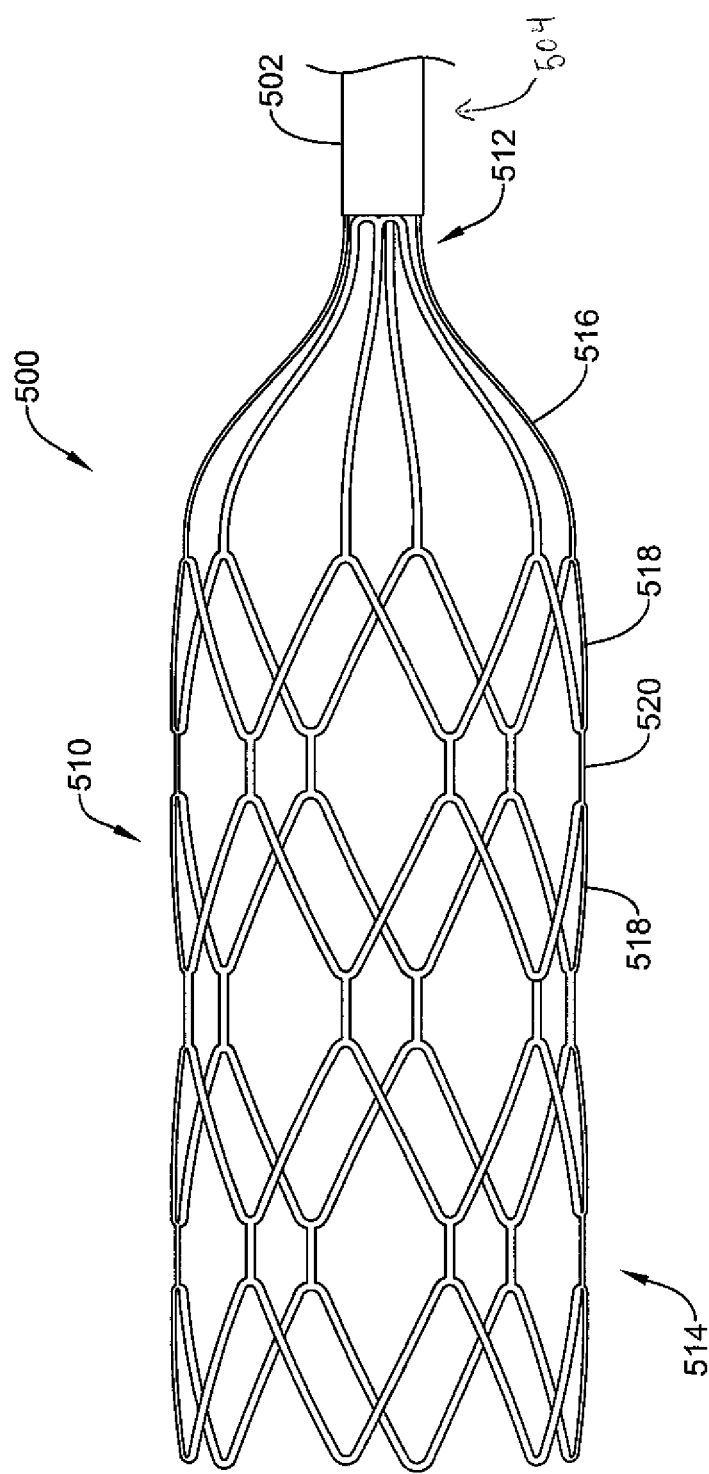
FIG. 5 is a side view of a distal portion of another illustrative expandable device.
Figure 6:
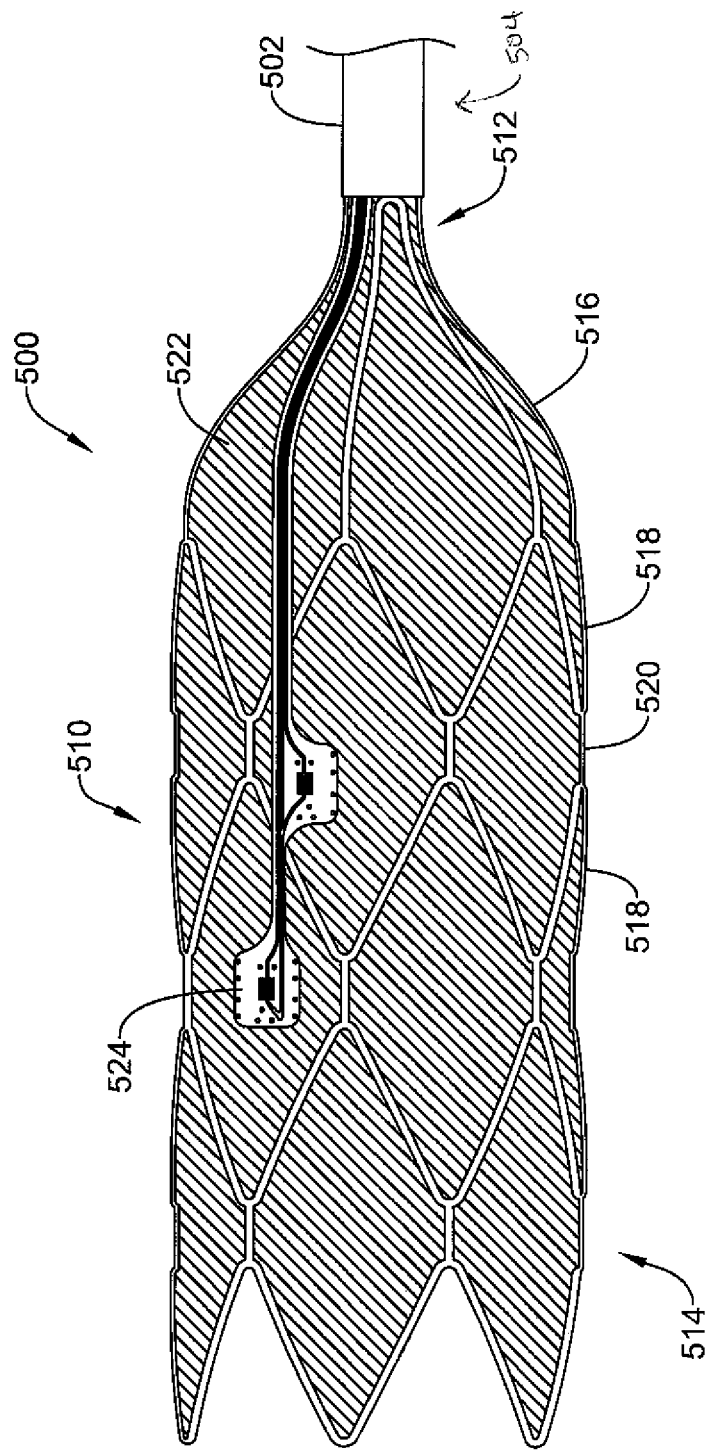
FIG. 6 is another side view of the illustrative expandable device of FIG. 5.

FIGS. 5 and 6 illustrate a distal portion of another illustrative nerve or tissue modulation or ablation device 500 having a basket or stent-like structure covered with a coating. The device 500 may include an elongate catheter shaft 502 having a proximal end (not shown) and a distal end region 504. The elongate shaft 502 may extend proximally from the distal end region 504 to the proximal end configured to remain outside of a patient's body. Although not shown, the proximal end of the elongate shaft 502 may include a hub attached thereto for connecting other treatment devices or providing a port for facilitating other treatments. It is contemplated that the stiffness of the elongate shaft 502 may be modified to form the modulation device 500 for use in various vessel diameters and various locations within the vascular tree.

In some instances, the elongate shaft 502 may have an elongate tubular structure and may include one or more lumens extending therethrough. In some embodiments, the elongate shaft 502 may include one or more guidewire or auxiliary lumens. In some instances, the elongate shaft 502 may include a separate lumen(s) (not shown) for infusion of fluids, such as saline or dye for visualization or for other purposes such as the introduction of a medical device, and so forth. The fluid may facilitate cooling of the modulation device 500 during the ablation procedure, in addition to the cooling of a body lumen. Further, the lumens may be configured in any way known in the art. For example, the lumen(s) may extend along the entire length of the elongate shaft 502 such as in an over-the-wire catheter or may extend only along a distal portion of the elongate shaft 502 such as in a single operator exchange (SOE) catheter. These examples are not intended to be limiting, but rather examples of some possible configurations. While not explicitly shown, the modulation device 500 may further include temperature sensors/wire, an infusion lumen, radiopaque marker bands, fixed guidewire tip, a guidewire lumen, and/or other components to facilitate the use and advancement of the device 500 within the vasculature.

Further, the elongate shaft 502 may have a relatively long, thin, flexible tubular configuration. In some instances, the elongate shaft 502 may have a generally circular cross-section, however, other suitable configurations such as, but not limited to, rectangular, oval, irregular, or the like may also be contemplated. In addition, the elongate shaft 502 may have a cross-sectional configuration adapted to be received in a desired vessel, such as a renal artery. For instance, elongate shaft 502 may be sized and configured to accommodate passage through an intravascular path, which leads from a percutaneous access site in, for example, the femoral, brachial, or radial artery, to a targeted treatment site, for example, within a renal artery.

The modulation device 500 may further include an expandable basket 510 having a proximal end region 512, a distal end region 514, and an optional bridge segment 516 disposed therebetween. In some instances, in the expanded state, the bridge segment 516 may span between a collapsed proximal end region 512 and the expanded distal end region 514. It is contemplated that the bridge segment 516 may be formed having a different pattern or structure than the proximal end region 512 or distal end region 514, as will be discussed in more detail below. In the expanded configuration (shown in FIG. 5), the distal end region 514 may have a larger, generally cylindrical, cross-sectional area than the proximal end region 512.

In some embodiments, the expandable basket 510 may be laser cut from a generally tubular member to form a desired pattern. While the expandable basket 510 is illustrated as having an open cell, generally stent-like, structure it is contemplated that the basket 510 may be formed to have any of a number of different configurations. In some embodiments, the expandable basket 510 may be formed from a plurality of interconnected circumferentially extending struts 518. The struts 518 may be connected by one or more connectors 520. It is contemplated that the struts 518 in combination with the connectors 520 may form a cellular configuration with each cell having any shape desired, such as, but not limited to: circular, square, oval, rectangular, polygonal, etc. In some instances, the basket 510 may be formed from a number of generally longitudinally extending tines or may be formed from one or more filaments that may be woven, braided, knotted, etc. These are just examples. It is further contemplated that while basket 510 is illustrated as including four struts 518 in the distal end region 514, the expandable basket 510 may include any number of struts 518 desired, such as, but not limited to, one, two, three, four, or more. It is further contemplated that the struts 518 may be spaced from the proximal end region 512 to the distal end region 514 as desired. Other illustrative basket assemblies useable with the embodiments disclosed herein are disclosed in U.S. patent application Ser. No. 14/512,020 entitled "Devices And Methods For Nerve Modulation", the full disclosure of which is incorporated by reference herein.

It is contemplated that the expandable basket 510 can be made from a number of different materials such as, but not limited to, metals, metal alloys, shape memory alloys and/or polymers, as desired, enabling the basket 510 to be expanded into shape when positioned within the body. For example, the expandable basket 510 can be formed from alloys such as, but not limited to, nitinol or Elgiloy®. Depending on the material selected for construction, the basket 510 may be self-expanding or may require an actuation mechanism as will be discussed in more detail below. In some embodiments, fibers may be used to make the expandable basket 510, which may be cored fibers, for example, having an outer shell made of nitinol having a platinum core. It is further contemplated that the expandable basket 510 may be formed from or partially from polymers including, but not limited to, polyether ether ketone (PEEK), nylon, polyethylene terephthalate (PET), polyimides, polyether block amides, etc. In some embodiments, the expandable basket 510 may further include radiopaque markers, bands or coatings.

The proximal end region 512 of the basket 510 may be secured to or adjacent to the distal end region 504 of the elongate shaft 502. As noted above, in some instances, the basket 510 may be self-expanding. It is contemplated that a self-expanding basket 510 may be maintained in a compressed (or collapsed state) when an external force is placed on the basket 510. The basket 510 may then expand when the external force is released. In such an instance, the basket 510 may be formed in the expanded state (as shown in FIG. 5) and compressed to fit within a delivery sheath. Upon reaching the target location, the delivery sheath can be retracted to deploy the expandable basket 510.

In other embodiments, the device 500 may include an actuation mechanism, for example, a pull wire (not explicitly shown), which may be employed to manipulate or actuate the expandable basket 510 between the collapsed and expanded configurations. In an embodiment, the pull wire may be attached to the proximal end region 512 of the basket 510 such that a push-pull actuation of the pull wire may manipulate the expandable basket 510, thus actuating the expandable basket 510 between the collapsed and expanded configurations.

In some embodiments, the expandable basket 510 may be formed from a conductive material covered with an insulating of semi-insulating coating. The expandable basket 510 may be coated with insulating material using any number of coating techniques, such as, but not limited to, dip coating, spray coating, etc. In some instances, the expandable basket 510 may be coated with parylene or other insulating material. In some instances, the coating may be formed of semi-insulating materials, such as but not limited to a porous polymer or a ceramic. It is further contemplated that the coating may be a very thin polymer or coating.

It is contemplated that the modulation device 500 may be advanced through the vasculature to a desired treatment region, such as the renal artery. The modulation device 500 may be advanced with the expandable basket 510 in a collapsed position. For example, the delivery sheath may be disposed over the basket 510 to maintain the basket 510 in a collapsed position. When the expandable basket 510 is positioned adjacent to the target treatment region, the delivery sheath may be retracted to allow at least a portion of the expandable basket 510 to contact a vessel wall. As discussed above, pull wires, or other actuation mechanisms can be used in place of or in combination with the delivery sheath to facilitate delivery of the device 500. In some embodiments, a guide catheter or vascular access catheter may be used in combination with the delivery sheath to facilitate advancement of the device 500. When the expandable basket 510 is in the expanded configuration, the proximal end region 512 may remain in a generally collapsed or low-profile configuration. In the expanded configuration, the outer surface of the expandable basket 510 may come into gentle contact with the vessel wall.

FIG. 6 illustrates the modulation system 500 of FIG. 5 including additional components. The modulation system 500 may further include an inner cover or coating 522 disposed on an inner surface of the expandable basket 510. In some instances, the inner cover 522 may be adhered to the basket 510 using methods commonly known in the art. The inner cover 522 may be made from an elastomeric material, such as, but not limited to: polyurethane, silicone, etc. An elastomeric material may help close the basket 510 to its un-expanded configuration after use. However, in some instances, elastomers such as polyurethane may fail due the heat from ablation. To prevent this, the elastomer could be insulated around the thermistors with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 522 may extend from the proximal end 512 to the distal end 514 of the basket 510. However, this is not required. It is contemplated that the inner cover 522 may extend over any length or partial length of the basket 510 desired, or may not even be present.

The modulation system 500 may further include one or more thermistor assemblies 524 positioned on a surface of the expandable basket 510 and/or inner cover 522 for delivering heat to a desired treatment region. The thermistor assembly 524 may be similar in form and function to the thermistor assemblies 300 described above. It is contemplated that the modulation system 500 may include any number of thermistor assemblies 524 desired based on the size of the modulation device 500 and/or the desired treatment region. For example, the modulation system may include one, two, three, four, five, or more thermistor assemblies. It is further contemplated that the thermistor assemblies 524 may be staggered about the circumference and/or length of the expandable basket 510 such that a maximum number of thermistor assemblies 524 can be positioned on the modulation device.

In some instances, one or more thermistor assemblies 524 may be positioned on or underneath a surface of an outer cover (not explicitly shown) positioned on an outer surface of the basket 510. It is contemplated that the outer cover may extend from the proximal end 512 to the distal end 514 of the basket 510. However, this is not required. It is contemplated that the outer cover may extend over any length or partial length of the basket 510 desired, or may not even be present. The inner 522 and outer covers may be formed of the same material or may be formed from different materials, as desired. In some embodiments, one or both of the inner 522 and/or outer covers may be omitted.

In some instances, the outer cover may be adhered to the inner cover 522 and/or basket 510 using methods commonly known in the art. Together, the inner 522 and outer covers may encase all or part of the thermistor assemblies 524 and the associated electronics. It is contemplated that the inner 522 and outer covers may fix the thermistor assemblies 524 more securely to the expandable basket 510 relative to securing assemblies to a traditional inflatable balloon as the inner 522 and outer covers sandwich the thermistor assemblies 524 and may be more amenable to covalent adhesive bonding. It is contemplated that affixing the thermistor assemblies 524 between at least the basket 510 and the outer cover may improve thermistor fixation to system since such an arrangement may eliminate or reduce thermistor catch points is not dependent on adhesive to fix the thermistor assemblies 524 to the modulation system. This may improve the safety of system 500.

When an outer cover is disposed over the thermistors, the thermistors may be in insulated contact with the desired treatment region. In some instances, the outer cover may not extend over the thermistors of the thermistor assemblies 524. For example, the thermistors may be coated or covered with a masking material prior to application of the outer cover. Once the outer cover has been formed, the masking material may be removed to expose the thermistors. In some instances, the outer cover may be disposed over the thermistors and subsequently removed with techniques, such as, but not limited to, laser ablation. This may allow for the thermistors to directly contact the vessel wall. It is further contemplated that the outer cover may be removed from some of the thermistors independently (for example using parylene) to allow for some insulated contact with the desired treatment region.

Figure 7:
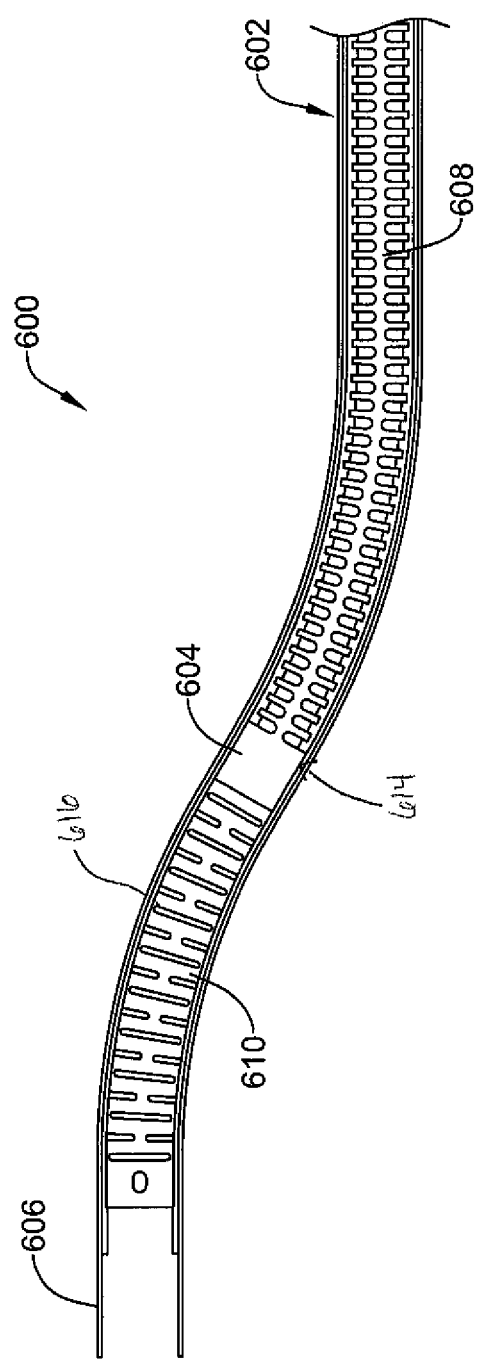
FIG. 7 is a partial cross-sectional side view of another illustrative catheter.
Figure 8:
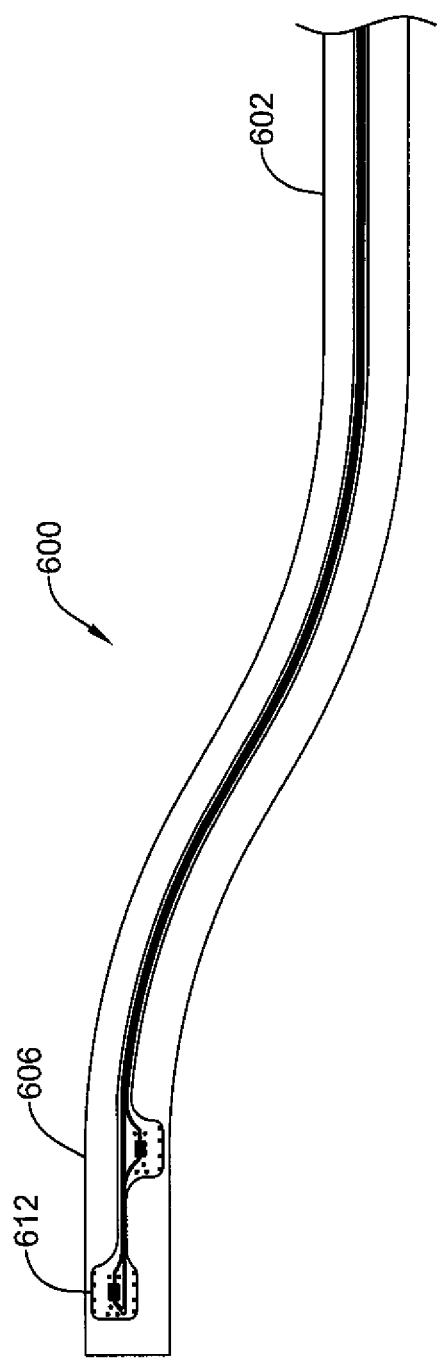
FIG. 8 is a side view of catheter of FIG. 8.

FIG. 7 is a partially cut away side view of an illustrative catheter 600. FIG. 8 is a side view of the illustrative catheter 600 of FIG. 7. Here, some of the structural features of the catheter 600 can be seen. For example, the catheter 600 may include a catheter shaft 602. The catheter shaft 602 may take the form of a metallic and/or polymer shaft and may include visualization (e.g., marker bands) and/or reinforcing structures (e.g., braids, coils, etc.) commonly used for catheter shafts. In at least some embodiments, the catheter shaft 602 may form or define an outer surface of the catheter 600. The catheter 600 may include one or more thermistor assemblies 612 affixed to an outer surface thereof adjacent to the distal end region 606, as shown in FIG. 8, for delivering heat to a desired treatment region. The thermistor assembly 612 may be similar in form and function to the thermistor assemblies 300 described above. It is contemplated that the catheter 600 may include any number of thermistor assemblies 612 desired based on the size of the catheter 600 and/or the desired treatment region. For example, the modulation system may include one, two, three, four, five, or more thermistor assemblies 612. It is further contemplated that the thermistor assemblies 612 may be staggered about the circumference and/or length of the catheter 600 such that a maximum number of thermistor assemblies 612 can be positioned on the modulation device.

When conducting a medical procedure that involves ablation or heating, it may be desirable to place the ablation member (e.g., thermistor assembly 612) near the target tissue so as to ablate the target while minimizing damage to non-targeted tissue. In order to more specifically place or steer catheter 600 to a position adjacent to the intended target, catheter 600 may be configured to be deflectable. Accordingly, catheter 600 may include a tubular member 614 that includes a flex body 608 that can be selectively bent. This allows a user to orient, for example, thermistor assembly 612 in a desirable position within a body lumen. To effect deflection, one or more pull wires or actuation members may be coupled to flex body 608. This allows a user to actuate (e.g., "pull") one or both of wires to deflect flex body 608 and, thus, catheter 600 (e.g., thermistor assembly 612). In addition, wires may be stiff enough so that they can also be used to provide a pushing force on flex body 608 to, for example, straighten flex body 608. In some instances, the actuation member may take the form of a continuous wire that is looped through or otherwise coupled to a distal end of flex body 608 so as to define a pair of wire section). In other instances, the actuation member may include one or more individual wires that are attached, for example, to the distal end of flex body 608.

To further aid in properly orienting catheter 600 within a body lumen, a flex tube 610 may be coupled to flex body 608 (e.g., at a distal end of flex body 608). Flex tube 610 may have a plurality of slots 616 formed therein. In general, flex tube 610 is configured to be flexible so that the distal portion of catheter 600 (e.g., adjacent to thermistor assembly 612) can bend upon encountering the wall of a body lumen. Accordingly, flex tube 610 can bend when/if thermistor assembly 612 engages the wall of the body lumen during deflection of flex body 608 so that thermistor assembly 612 may atraumatically follow along the wall of the body lumen.

In at least some embodiments, flex body 608 and flex tube 610 are two distinct structures that are attached to one another. In other embodiments, flex body 608 and flex tube 610 are formed in tubular member 614 by selectively cutting the desired pattern into tubular member 614. For example, tubular member 614 may be cut in a first pattern that defines flex body 608 and tubular member 614 may be cut in a second pattern that defines flex tube 610. The cut patterns may be substantially continuous (e.g., where relatively little or no appreciable spacing is defined between the patterns) or the patterns may be longitudinally spaced so that a gap is defined therebetween. Analogously, flex body 608 and flex tube 610 may be substantially continuous with one another or longitudinally spaced from one another so that an intermediate region 604 is defined therebetween. In some embodiments flex body 608 and flex tube 610 may be formed from a nickel-titanium alloy, such as, but not limited to, nitinol, although this is not required. It is contemplated that flex body 608 and flex tube 610 may be formed from any material desired.

Catheter 600 may also include a number of additional features commonly associated with medical devices. For example, catheter 600 may include radiopaque markers or bands, additional or alternative catheter shaft constructions (e.g., having lumens, reinforcements, balloons, or other catheter structures), a proximal hub and strain relief, and the like.

FIG. 7 illustrates the catheter 600 in a deflected configuration. Here it can be seen how flex body 608 (and flex tube 610) can aid in the orientation of catheter 600 within a blood vessel. In this example, a pull wire may be actuated to cause flex body 608 to bend. This thermistor assembly 612 toward the wall of blood vessel 40. Flex tube 610 allows catheter 600 to further bend so that thermistor assembly 612 can trace along and lay flat against the wall of blood vessel or desired treatment region. Other illustrative catheters useable with the embodiments disclosed herein are disclosed in U.S. patent application Ser. No. 14/366,692 entitled "Deflectable Medical Devices", the full disclosure of which is incorporated by reference herein.

Figure 9:
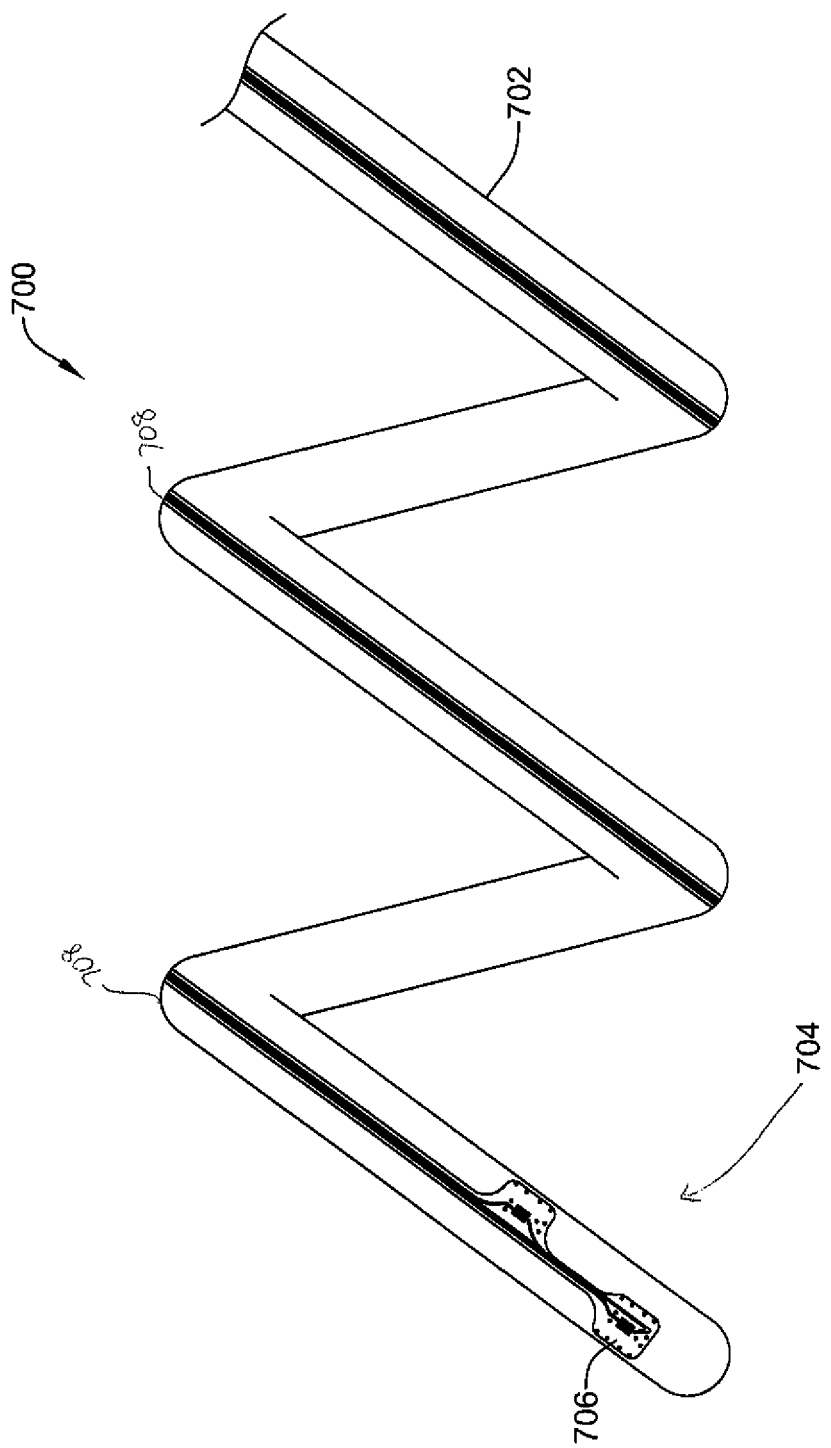
FIG. 9 is a side view of another illustrative catheter.

FIG. 9 illustrates a distal portion of another illustrative catheter 700 for use in a modulation or ablation system. Here, some of the structural features of the catheter 700 can be seen. For example, the catheter 700 may include a catheter shaft 702. The catheter shaft 702 may take the form of a metallic and/or polymer shaft and may include visualization (e.g., marker bands) and/or reinforcing structures (e.g., braids, coils, etc.) commonly used for catheter shafts. In at least some embodiments, the catheter shaft 702 may form or define an outer surface of the catheter 700. The catheter 700 may include one or more thermistor assemblies 706 affixed to an outer surface thereof adjacent to the distal end region 704 for delivering heat to a desired treatment region. The thermistor assembly 706 may be similar in form and function to the thermistor assemblies 300 described above. It is contemplated that the catheter 700 may include any number of thermistor assemblies 706 desired based on the size of the catheter 700 and/or the desired treatment region. For example, the modulation system may include one, two, three, four, five, or more thermistor assemblies 706. It is further contemplated that the thermistor assemblies 706 may be staggered about the circumference and/or length of the catheter 700 such that a maximum number of thermistor assemblies 706 can be positioned on the modulation device.

The elongate shaft 702 may extend proximally from the distal end region 704 to the proximal end configured to remain outside of a patient's body. Although not shown, the proximal end of the elongate shaft 702 may include a hub attached thereto for connecting other treatment devices or providing a port for facilitating other treatments. It is contemplated that the stiffness of the elongate shaft 702 may be modified to form the modulation device 700 for use in various vessel diameters and various locations within the vascular tree.

In some instances, the elongate shaft 702 may have an elongate tubular structure and may include one or more lumens extending therethrough. In some embodiments, the elongate shaft 702 may include one or more guidewire or auxiliary lumens. In some instances, the elongate shaft 702 may include a separate lumen(s) (not shown) for infusion of fluids, such as saline or dye for visualization or for other purposes such as the introduction of a medical device, and so forth. The fluid may facilitate cooling of the modulation device 700 during the ablation procedure, in addition to the cooling of a body lumen. Further, the lumens may be configured in any way known in the art. For example, the lumen(s) may extend along the entire length of the elongate shaft 702 such as in an over-the-wire catheter or may extend only along a distal portion of the elongate shaft 702 such as in a single operator exchange (SOE) catheter. These examples are not intended to be limiting, but rather examples of some possible configurations. While not explicitly shown, the modulation device 700 may further include temperature sensors/wire, an infusion lumen, radiopaque marker bands, fixed guidewire tip, a guidewire lumen, and/or other components to facilitate the use and advancement of the device 700 within the vasculature.

Further, the elongate shaft 702 may have a relatively long, thin, flexible tubular configuration. In some instances, the elongate shaft 702 may have a generally circular cross-section, however, other suitable configurations such as, but not limited to, rectangular, oval, irregular, or the like may also be contemplated. In addition, the elongate shaft 702 may have a cross-sectional configuration adapted to be received in a desired vessel, such as a renal artery. For instance, elongate shaft 702 may be sized and configured to accommodate passage through an intravascular path, which leads from a percutaneous access site in, for example, the femoral, brachial, or radial artery, to a targeted treatment site, for example, within a renal artery.

The distal end region 704 of the elongate shaft 702 may generally take the form or be configured to take the form of a helix including a plurality of windings or rings 708. For example, the elongate shaft 702 may include a combination of pull wires or actuation members and flexible members, such as, but not limited to, flex body 608 and/or flex tube 610 described above, that can be selectively bent. This may allow the elongate shaft 702 to be advanced to a desired treatment region in a relatively straight configuration and selectively bent by the user to achieve the desired configuration. Alternatively, or additionally, the distal end region 704 may be formed of shape memory materials such as shape memory alloys and/or shape memory polymers. This may allow the distal end region 704 of the elongate shaft 702 to be formed having a generally helically shape. The elongate shaft 702 may be may be maintained in a compressed (or generally straightened state) when an external force is placed on the distal end region 704. The distal end region 704 may then expand and resume its generally helical shape when the external force is released. In such an instance, the distal end region 704 may be formed in the generally helical shape (as shown in FIG. 9) and compressed to fit within a delivery sheath. Upon reaching the target location, the delivery sheath can be retracted to deploy the distal end region 704. It is further contemplated that the distal end region 704 may assume its helical shape upon the application of an external stimulus, such as, but not limited to, heat.

In other embodiments, the elongate shaft 702 may be configured to be advanced to the target treatment region with the distal end region 704 in the generally helical configuration.

The size (outer diameter) and spacing (pitch) of the rings 708 may be varied, as desired. It is contemplated that the distal end region 704 may include any number of rings desired, such as, but not limited to, one, two, three, four, or more. For example, the rings 708 may be sized such that they are configured to come into contact with or be brought into contact with a vessel or target tissue. This may allow the thermistor assembly 706 to come into contact with the tissue to be treated, or tissue adjacent thereto. It is contemplated that the distal end region 704 may include a plurality of circumferentially and longitudinally spaced thermistor assemblies 706. This may allow for simultaneous treatment of a plurality of discrete locations about the circumference and length of a treatment zone.

A method of modulating a nerve disposed within the vessel wall is disclosed herein. The method includes inserting a medical device within a body lumen (e.g., vessel, renal artery, etc.) to provide heat therapy or treatment. While the method is described with respect to a balloon catheter, it is contemplated that any of the devices described herein, such as modulation devices 400, 500 and catheters 600, 700, may be used in a similar manner. The medical device may include a balloon catheter with a balloon disposed on a distal end of the balloon catheter. The balloon may include a balloon wall and the balloon may be configured to transition between an expanded state and a collapsed state. During insertion and navigation through a vessel lumen (e.g., a body lumen, blood vessel, etc.), the balloon may be in the collapsed state. Once the medical device is advanced to a treatment location (e.g., inside a vessel lumen, etc.), the balloon may be inflated using an inflation fluid (e.g., air, saline, etc.) such that upon inflation, one or more thermistors disposed on the balloon wall may come in contact with target tissue (e.g. a vessel wall near at least one nerve) to be modulated or treated. The balloon 30 may be transitioned from the collapsed state to the expanded state in any of a large variety of methods. For example, in one or more embodiments, the balloon 30 may be inflated with inflation fluid entering the balloon 30 via the lumen from an inflation fluid source located outside a patient's body.

The balloon catheter 30 discussed above in one or more embodiments of the present disclosure may have a tubular state with a circular cross-section. However, a person skilled in the art will appreciate that other suitable cross-sections such as rectangular, oval, irregular or the like may also be contemplated. In one or more embodiments, the state and the cross-section of the balloon catheter 30 may be suitably dimensioned and configured to accommodate passage through a vessel lumen (e.g., a blood vessel, etc.).

In use, the medical device may be advanced through a blood vessel or body passageway to a position adjacent to a target tissue (e.g., within a renal artery), in some cases with the aid of a delivery sheath or catheter. In some embodiments, the target tissue may be one or more sympathetic nerves disposed about the blood vessel. In some embodiments, a control unit may be operationally coupled to the medical device, which may be inserted into a blood vessel or body passageway such that balloon (having a thermistor or thermistor array) may be placed adjacent to the target tissue where therapy is required. Placement of the thermistor or thermistor array adjacent the target tissue where therapy is required may be performed according to conventional methods, (e.g., over a guidewire under fluoroscopic guidance). When suitably positioned, the balloon may be expanded from a collapsed delivery configuration to an expanded configuration, for example by pressurizing fluid to about 1-10 atmospheres (atm) in the case of a balloon. This may place/urge the thermistor (e.g., thermistor array) against the wall of the blood vessel. The thermistor (e.g., thermistor array) may be activated.

The thermistor(s) may be a hot end thermistor in which the thermistor can both heat the target tissue to a desired temperature and provide feedback to a power and control unit, such as the source of electric current 10, regarding the current temperature of the thermistor and/or the temperature of the tissue adjacent to the thermistor. For example, as the temperature of the thermistor increases or decreases, the resistance of the thermistor will change. A power and control unit or other monitoring device, may determine the temperature of the thermistor based on the measured resistance. It is contemplated that the power and/or frequency of the electrical current supplied to the thermistor can be adjusted to achieve the desired temperature either manually by a clinician or automatically by the power and control unit. For example, the power and control unit may be programmed with a control algorithm configured to control the power, frequency, or other parameters of the electrical current to achieve a desired treatment temperature or temperature profile.

In some embodiments, the thermistor may be made from a Curie temperature material. In addition to heating the target tissue and providing feedback regarding the current temperature, a Curie temperature thermistor may also provide an upper limit on how hot the thermistor can get. For example, the thermistor may heat only in the presence of a specified electric or magnetic field and frequency and only to the Curie temperature of the thermistor. When the Curie temperature is reached, the material goes from magnetic to non-magnetic, discontinuing the heating. This is a cyclic process that permanently and rapidly maintains the thermistor temperature at the set Curie point of the material, as long as the electric or magnetic field is applied. In some instances, an electromagnetic coil or magnetic generator may be provided within or on the device to generate a magnetic field in close proximity to the Curie temperature material. The power and control unit may supply electrical energy to the electromagnetic coil to generate the magnetic field.

Heat may be transmitted from the thermistor or thermistor array through the target tissue (where sympathetic nerves may be ablated, modulated, or otherwise impacted). Following treatment, the balloon may be collapsed to the collapsed delivery configuration for retraction into a guide sheath or catheter and subsequent withdrawal from the blood vessel or body passageway.

In one or more embodiments, the control unit 10 is operationally coupled to the catheter device 20, which may be placed in a body passageway such that an expandable device 30 (having thereon a plurality of thermistor assemblies) is placed adjacent to a first section (e.g., lengthwise section) of the body passageway where therapy is desired. Placement of the catheter device at the first section can be performed according to conventional methods, e.g., over a guidewire under fluoroscopic guidance. Once placed in the first section, the expandable device can be made to expand, e.g., by inserting pressurizing fluid into the expandable device at a pressure from 1-10 atm, in the case of a balloon. This causes thermistor assemblies of the expandable device 30 to come into contact with the body passageway. One or more methods of treating multiple sections of a body passageway are described by Mathur et al. (WO 2013/096919 A1) at pages 60-61.

Depending on the particular remodeling effect desired, the control unit may energize the thermistors with about 0.25 to 5 Watts average power for 1 to 180 seconds, or with about 0.25 to 900 Joules. Higher energy treatments may be done at lower powers and longer durations, such as 0.5 Watts for 90 seconds or 0.25 Watts for 180 seconds. In an example embodiment for use in renal denervation, energy is delivered for about 30 seconds at a treatment setting of about 5 Watts, such that treatment zones are heated to about 58° C. during treatment. In one or more embodiments, treatment zones are heated to about 68° C. As stated above, power requirements may depend heavily on thermistor configuration. Generally, with wider thermistor spacing, more power is required, in which case the average power could be higher than 5 Watts, and the total energy could exceed 45 Joules. Likewise, using a shorter or smaller distance between thermistors would require scaling the average power down, and the total energy could be less than 4 Joules. The power and duration may be, in some instances, calibrated to be less than enough to cause severe damage, and particularly less than enough to ablate diseased tissue within a blood vessel. The mechanisms of ablating atherosclerotic material within a blood vessel have been well described, including by Slager et al. in an article entitled, "Vaporization of Atherosclerotic Plaque by Spark Erosion" in J. of Amer. Cardiol. (June, 1985), on pp. 1382-6; and by Stephen M. Fry in "Thermal and Disruptive Angioplasty: a Physician's Guide"; Strategic Business Development, Inc., (1990), the full disclosure of each of which is incorporated herein by reference.

The application of energy (e.g., A/C current, D/C current, RF energy, etc.) can be controlled so as to limit a temperature of target and/or collateral tissues, for example, limiting the heating of target tissue such that neither the target tissue nor the collateral tissue sustains irreversible thermal damage. In one or more embodiments, the treatment temperature is at least 30° C. (e.g., at least 50° C., at least 70° C., from 50° C. to 90° C., from 50° C. to 70° C., from 70° C. to 90° C., etc.). In some embodiments, the range of surface temperatures (of the device) is from about 50° C. to about 90° C. For gentle heating, the surface temperature may range from about 50° C. to about 70° C., while for more aggressive heating, the surface temperature may range from about 70° C. to about 90° C. Limiting heating so as to inhibit heating of collateral tissues to less than a surface temperature in a range from about 50° C. to about 70° C., such that the bulk tissue temperature remains mostly below 50° C. to 55° C., may inhibit an immune response that might otherwise lead to stenosis, thermal damage, or the like. Relatively mild surface temperatures between 50° C. and 70° C. may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

In some embodiments, the target temperature may vary during the treatment, and may be, for instance, a function of treatment time. For example, one possible target temperature profile, among many suitable target temperature profiles, for a treatment with a duration of 30 seconds may include a twelve-second ramp up from nominal body temperature to a maximum target temperature of about 68° C. In one or more embodiments, a gradual decrease in the rate of temperature increase as the temperature approaches the target temperature (e.g., 68° C., etc.) may facilitate reducing overshoot and/or undershoot of the set target temperature for the remainder of the treatment. Additional temperature profiles that may be useful in one or more embodiments are disclosed by Mathur et al. (WO 2013/096919 A1).

The materials that can be used for the various components of medical device (and/or other devices disclosed herein) may include those commonly associated with medical devices. For simplicity purposes, the following discussion makes reference to the medical device. However, this is not intended to limit the devices and methods described herein, as the discussion may be applied to other similar tubular members and/or expandable members and/or components of tubular members and/or expandable members disclosed herein.

The medical device and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polyvinylidene fluoride, poly (styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments a sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure, linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials, such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel.

One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, each of which is incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the medical device may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device in determining its location. Some examples of radiopaque materials can include, but are not limited to, gold, platinum, palladium, tantalum, tungsten, and alloys thereof, titanium dioxide, bismuth subcarbonate, platinum and barium sulphate, platinum iridium, platinum tungsten, polymer material loaded with a radiopaque filler, and the like. Additionally, other radiopaque marker bands and/or coils may also be incorporated into the design of the medical device to achieve the same result.

In some embodiments, a degree of Magnetic Resonance Imaging (MRI) compatibility may be imparted into the medical device. For example, portions of device may be made of a material that does not substantially distort the image and create substantial artifacts (e.g., gaps in the image). Certain ferromagnetic materials, for example, may not be suitable because they may create artifacts in an MRI image. In some of these and in other embodiments, portions of the medical device may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A description of some exemplary embodiments of the present disclosure is contained in one or more of the following numbered statements:

Statement 1. A medical device for nerve modulation, the medical device comprising:
a balloon catheter comprising a balloon structured and arranged to be disposed within a vessel that defines a vessel lumen, wherein the balloon comprises a balloon wall;
at least one thermistor array disposed on the balloon wall, the at least one thermistor array comprising at least two thermistors and being operatively engaged with a source of electric current, each of the at least two thermistors having a resistance that varies with temperature, and
wherein the medical device is configured and arranged to transfer heat to the medical device surroundings and wherein at least 50 percent of the heat transferred from the medical device to the medical device surroundings is generated by resistance heating.

Statement 2. The medical device of statement 1, wherein the source of electric current is at least one of radio frequency, alternating current, and direct current.

Statement 3. The medical device of statement 1 or statement 2, wherein at least 90 percent of the heat transferred from the medical device to the medical device surroundings is generated by resistance heating of one or more thermistors.

Statement 4. The medical device of any one of statements 1-3, wherein the at least one thermistor array operatively engaged with a source of electric current comprises a first wire extending from the source of electric current to the at least one thermistor array and a second wire extending from the at least one thermistor array to a ground.

Statement 5. The medical device of any one of statements 1-4, wherein the at least one thermistor array is associated with an independent ground.

Statement 6. The medical device of any one of statements 1-5, wherein each of the at least two thermistors is associated with an independent ground.

Statement 7. The medical device of any one of statements 1-4, wherein the at least two thermistors are associated with a shared ground.

Statement 8. The medical device of any one of statements 1-7, wherein the at least one thermistor array comprises at least three thermistors.

Statement 9. The medical device of any one of statements 1-8, wherein the at least one thermistor array comprises at least a first plurality of thermistors, wherein each of the first plurality of thermistors is disposed at a first longitudinal distance from a proximal end of the balloon.

Statement 10. The medical device of statement 9, wherein the thermistor array comprises at least a second plurality of thermistors, wherein each of the second plurality of thermistors is disposed at a second longitudinal distance from the proximal end of the balloon.

Statement 11. The medical device of statement 9, wherein the first plurality of thermistors are evenly distributed about a balloon circumference.

Statement 12. A device, comprising:
an expandable balloon including an outer surface and defining a balloon longitudinal axis extending from a proximal end to a distal end of the expandable balloon; and
at least one flexible circuit mounted on the outer surface of the expandable balloon, the at least one flexible circuit comprising:
a first insulating layer;
a second insulating layer above the conductive layer, and
a conductive layer between the first insulating layer and the second insulating layer;
at least one temperature-sensing device comprising at least one thermistor, wherein at least a portion of the conductive layer is electronically coupled to the thermistor;
with the proviso that no electrode is associated with the conductive layer.

Statement 13. The device of statement 12, wherein the at least one thermistor is positioned at least partially within the first insulating layer.

Statement 14. The device of statement 12 or statement 13, wherein the at least one thermistor has a thickness of less than approximately 0.15 millimeters.

Statement 15. The device of any one of statements 12-14, wherein a material having increased thermal conductivity relative to the second insulating layer is positioned at least partially within the second insulating layer and is in contact with the at least one thermistor.

Statement 16. The device of any one of statements 12-15, wherein the at least one flexible circuit comprises at least a plurality of thermistors that are arranged along a first longitudinal axis approximately parallel to the balloon longitudinal axis.

Statement 17. The device of any one of statements 12-16, wherein the at least one temperature-sensing device is structured and arranged to measure a temperature representative of an outer surface of at least a portion of the flexible circuit.

Statement 18. A method of nerve modulation comprising:
receiving a medical device comprising:
a balloon catheter comprising a balloon structured and arranged to be disposed within a vessel that defines a vessel lumen, wherein the balloon comprises a balloon wall; and
at least one thermistor array disposed on the balloon wall, the at least one thermistor array comprising at least two thermistors and being operatively engaged with a source of electric current, each of the at least two thermistors having a resistance that varies with temperature;
disposing the at least one thermistor array proximate a nerve to be modulated; and transferring heat from the medical device to the nerve to modulate the nerve, wherein at least 50 percent of the heat transferred from the medical device is generated by resistance heating.

Statement 19. The method of statement 18, wherein transferring heat from the medical device comprises heating the at least two thermistors.

Statement 20. The method of statement 18 or statement 19, wherein transferring heat from the medical device comprises monitoring temperature of the at least two thermistors by measuring electrical resistance.

Statement 36. A medical device comprising:
a balloon;
a thermistor disposed on the balloon;
wherein the thermistor is configured and arranged to increase in temperature to a treatment temperature, upon delivery of an electric current thereto, and wherein a temperature of the thermistor may be determined via a determination of an electrical resistance of the thermistor.

Statement 37. The medical device of statement 36 wherein the treatment temperature is at least 30 degrees Celsius.

Statement 38. The medical device of statement 36 or statement 37, wherein the increase in temperature is due primarily to resistive heating of the thermistor.

Statement 39. The medical device of any one of statements 36-38 wherein the electric resistance of the thermistor is converted to temperature based on a predetermined relationship between the temperature and electric resistance of the thermistor.

Statement 40. The medical device of any one of statements 36-39 further comprising a source of electric current electrically coupled to the thermistor and a resistance-determining device configured to determine the resistance of the thermistor.

Statement 41. The medical device of statement 40 wherein the source of electric current is electrically coupled to the thermistor in an electrical circuit comprising one or more conductive traces and wherein the resistance-determining device is an ohmmeter.

It should be understood that this disclosure is, in many respects, only illustrative. Changes may be made in details (e.g., matters of shape, size, and arrangement of components and/or steps) without exceeding the scope of the present disclosure. This may include, to the extent that it is appropriate, the use of any of the features of one embodiment being used in one or more other embodiments.

What is claimed is:

1. A device, comprising:
an expandable device including an outer surface and defining a longitudinal axis extending from a proximal end to a distal end of the expandable device; and
at least one flexible circuit mounted on the outer surface of the expandable device, the at least one flexible circuit comprising:
a conductive layer;
a first insulating layer;
a second insulating layer above the conductive layer, and the conductive layer between the first insulating layer and the second insulating layer; and
at least one thermistor that both senses temperature and generates heat, wherein at least a portion of the conductive layer is electronically coupled to the thermistor, with the proviso that no electrode external to the conductive layer is associated with the conductive layer.

2. The device of claim 1, wherein the at least one thermistor is positioned at least partially within the first insulating layer.

3. The device of claim 1, wherein the at least one thermistor has a thickness of less than approximately 0.15 millimeters.

4. The device of claim 1, wherein a material having increased thermal conductivity relative to the second insulating layer is positioned at least partially within the second insulating layer and is in contact with the at least one thermistor.

5. The device of claim 1, wherein the at least one flexible circuit comprises at least a plurality of thermistors that are arranged along a first longitudinal axis approximately parallel to the balloon longitudinal axis.

6. The device of claim 1, wherein the thermistor is structured and arranged to measure a temperature representative of an outer surface of at least a portion of the flexible circuit.

* * * * *